United States Patent [19]

Wolf

[11] 4,213,773
[45] Jul. 22, 1980

[54] HERBICIDAL SUBSTITUTED BICYCLIC TRIAZOLES

[75] Inventor: Anthony D. Wolf, Newark, Del.

[73] Assignee: E. I. Du Pont de Nemours and Company, Wilmington, Del.

[21] Appl. No.: 851,731

[22] Filed: Nov. 17, 1977

Related U.S. Application Data

[63] Continuation-in-part of Ser. No. 758,996, Jan. 13, 1977, abandoned.

[51] Int. Cl.$^2$ .................. A01N 9/22; C07D 471/04; C07D 487/04
[52] U.S. Cl. .................. 71/92; 260/239 B; 260/326.86; 546/119; 546/223
[58] Field of Search .................. 260/293.55, 308 C; 71/92; 546/119

[56] References Cited

U.S. PATENT DOCUMENTS

| | | | |
|---|---|---|---|
| 4,046,552 | 9/1977 | Davies et al. | 71/92 |
| 4,139,364 | 2/1979 | Wolf | 71/92 |

FOREIGN PATENT DOCUMENTS 811765 8/1959 United Kingdom .................. 546/82

OTHER PUBLICATIONS

Suzuki, S. et al., *Fifth Asian Pacific Weed Science Society Conference,* Tokyo, Oct. 1975, Paper No. 39, p. 40.

*Primary Examiner*—John M. Ford
*Assistant Examiner*—Richard A. Schwartz

[57] ABSTRACT

Substituted bicyclic triazole compounds essentially as shown in Formula I, agricultural compositions containing them, and the method of use of these compounds as herbicides for the control of undesired vegetation in crops

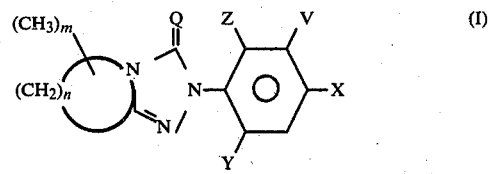

64 Claims, No Drawings

HERBICIDAL SUBSTITUTED BICYCLIC TRIAZOLES

CROSS REFERENCE TO RELATED APPLICATION

This application is a continuation-in-part of my application Ser. No. 758,996, filed January 13, 1977, now abandoned.

BACKGROUND OF THE INVENTION

German Offenlegungsschrift No. 1,957,783 discloses amidrazones (a) and states they are useful as antihypertensives.

(a)

wherein $R_1$, $R_2$ and $R_3$ are hydrogen, fluorine, chlorine, bromine, trifluoromethyl or alkyl of 1-3 carbon atoms; and n is 3, 4 or 5.

Belgium Pat. Nos. 802,446 and 802,447 disclose substituted arylamidrazones (b) as fungicides.

(b)

wherein X may be fluorine, chlorine, bromine, iodine, nitro, methoxy, ethoxy, methylthio, dimethylamino, trifluoromethyl or methylsulfonyl; and n may be 3, 4 or 5.

DESCRIPTION OF THE INVENTION

This invention relates to novel substituted bicyclic triazoles of Formula I, to agricultural compositions containing them, and to the method of use of these compounds as herbicides for the control of undesired vegetation in major crops, e.g. corn, sugar beets and wheat (I)

wherein:
V is hydrogen, fluorine, chlorine, bromine, hydroxy, alkyl of 1-4 or -$OR_1$ wherein:
  $R_1$ is alkyl of 1-6 optionally substituted with 1-3 fluorines, chlorines or bromines, cycloalkyl of 4-6, cycloalkyalkyl of 4-7, alkenyl of 3-6 optionally substituted with 1-3, fluorines, chlorines or bromines, alkynyl of 3-6, $CHR_7R_8$ or $$-CH{-}\underset{R_2}{\overset{}{\bigcirc}}{-}R_3, \quad -\overset{O}{\underset{}{C}}{-}N\underset{R_5}{\overset{R_4}{<}}, \quad -\overset{O}{\underset{}{C}}R_6$$

wherein:
$R_2$ is hydrogen or methyl;
$R_3$ is hydrogen, chlorine, bromine, methyl or methoxy;
$R_4$ is alkyl of 1-4;
$R_5$ is hydrogen, methyl or methoxy;
$R_6$ is alkyl of 1-4 or alkoxy of 1-4;
$R_7$ is hydrogen or alkyl of 1-4;

$CO_2R_9$, $CH_2OR_9$, $CH_2-O\overset{O}{\overset{\|}{C}}R_{10}$, CN, $-\overset{O}{\overset{\|}{C}}CH_3$, $-CH=CH\overset{O}{\overset{\|}{C}}R_9$, or $-\overset{O}{\overset{\|}{C}}N\overset{R_{11}}{\underset{R_{12}}{<}}$ $R_9$ is hydrogen or alkyl of 1-4;
$R_{10}$ is alkyl of 1-3;
$R_{11}$ is hydrogen, alkyl of 1-4, alkenyl of 3-4 or alkoxy of 1-2; and
$R_{12}$ is hydrogen or alkyl of 1-2
X is fluorine, chlorine, bromine, cyano, methyl, methoxy or nitro;
Y is hydrogen, fluorine, chlorine, bromine or methyl;
Z is hydrogen, fluorine, chlorine or bromine;
n is 3, 4 or 5;
m is 0, 1 or 2; and
Q is oxygen or sulfur;
provided that
  (1) When V is other than hydrogen, Y must be other than hydrogen;
  (2) When m is 1, n is 4 and Y must be other than hydrogen;
  (3) When m is 2, n is 4, X and Y are chlorine and V is $-OR_1$ wherein $R_1$ is alkyl of 1-4;
  (4) When Q is sulfur, m is 0;
and their agriculturally suitable salts.

Preferred for their high herbicidal activity and/or favorable cost are those compounds of Formula I as defined above where independently or in combination
V is hydrogen, fluorine, chlorine, bromine, hydroxy, methyl or $-OR_1$
X is fluorine, chlorine, bromine, methyl or nitro;
Y is fluorine, chlorine, bromine or methyl;
Z is hydrogen, fluorine or chlorine;
n is 4 or 5; and
m is 0

More preferred for their higher herbicidal activity and/or more favorable cost are those compounds which are preferred above where independently or in combination
V is hydrogen, chlorine, bromine or -$OR_1$ wherein: $R_1$ is alkyl of 1-4;
X is fluorine, chlorine or bromine; and
Z is hydrogen Most preferred for their even higher herbicidal activity and/or exceptionally favorable cost are those compounds which are more preferred above wherein; n is 4.

Most highly preferred for their outstanding herbicidal activity and/or highly favorable cost are those compounds which are most preferred above, where independently or in combination V is hydrogen, chlorine or -OR$_1$;

X is chlorine or bromine; and

Y is fluorine, chlorine or bromine

In particular the combination is most highly preferred.

Specifically preferred for their very outstanding herbicidal activity and/or very highly favorable cost are:

2-(2,4-dichloro-5-hydroxyphenyl)-5,6,7,8-tetrahydro-1,2,4-triazolo[4,3-A]pyridin-3(2H)-one, m.p. 211°–212°

2-(2,4-dichloro-5-propargyloxyphenyl)-5,6,7,8-tetrahydro-1,2,4-triazolo[4,3-A]pyridin-3(2H)-one, m.p. 167°–169°

2-[2,4-dichloro-5-(1-methylethoxy)phenyl]-5,6,7,8-tetrahydro-1,2,4-triazolo[4,3-A]-pyridin-3(2H)-one (oil)

2-(2,4-dichloro-5-methoxyphenyl)-5,6,7,8-tetrahydro-1,2,4-triazolo[4,3-A]-pyridin-3(2H)-one, m.p. 160°–163° C.

2-(2,4-dichloro-5-ethoxyphenyl)-5,6,7,8-tetrahydro-1,2,4-triazolo[4,3-A]-pyridin-3(2H)-one, m.p. 130°–132° C.

2-[2,4-dichloro-5-(1-methylethoxy)phenyl]-2,5,6,7,8,9-hexahydro-3H-1,2,4-triazolo[4,3-A]-azepin-3-one (oil)

SYNTHESIS OF THE COMPOUNDS

The compounds of this invention may be synthesized as shown in Equations A through G

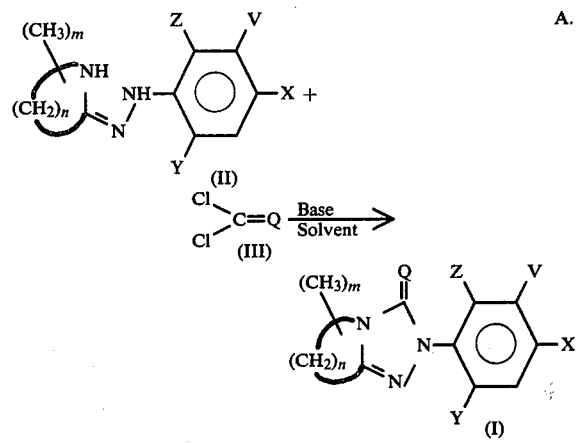

The conversion of the amidrazones II, or their acid salts (e.g. hydrochlorides), to the compounds of Formula I is accomplished by reaction with either phosgene (Q in Formula III is oxygen) which yields the compounds of Formula I wherein Q is oxygen, or thiophosgene (Q in Formula III is sulfur) which yields the compounds of Formula I wherein Q is sulfur. The reaction is run in a suitable inert organic solvent, e.g. an aromatic hydrocarbon such as benzene or toluene, a chlorinated alkane such as chloroform or methylene chloride, or an ether-type solvent such as tetrahydrofuran. In order to neutralize the acid liberated during the reaction, a suitable base is used, such as a tertiary amine, e.g. pyridine or triethylamine (with hydrocarbon solvents, e.g. toluene or xylene a base is not necessary). Ordinary precautions are taken to exclude moisture from the reaction. For completion of the reaction, it is sometimes necessary to heat the reaction mixture to reflux for a period of one to 24 hours. The product of the reaction is isolated by pouring the reaction mixture into water and extracting the product with a suitable solvent, e.g. ether or methylene chloride. The organic extract of the product is dried by addition of a drying agent, e.g. anhydrous sodium sulfate, and the solvent is removed by distillation or evaporation at reduced pressure, leaving the crude product. Purification of the crude material is accomplished by standard techniques, e.g. crystallization, chromatography or distillation.

Compounds of Formula I, wherein Q is oxygen can be prepared readily by the process shown in Equation B.

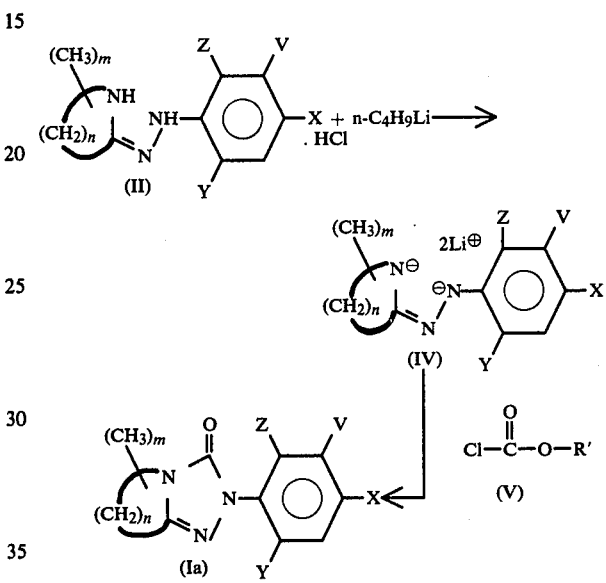

The amidrazone acid salt II in a suitable solvent, e.g. anhydrous tetrahydrofuran, is reacted with three equivalents of n-butyllithium which generates the amidrazone dianion IV. If the amidrazone free base is used, only two equivalents of n-butyllithium are necessary to generate the dianion IV. Otherwise, in each of the reactions according to Equation B, the same conditions can be used. The reaction temperature is maintained between −10° and 10° C. After the addition of n-butyllithium is completed, the reaction is stirred for a brief period (e.g. between 5 and 30 minutes) while maintaining the temperature. One equivalent of an alkyl chloroformate wherein R' is an alkyl group of 1 to 3 carbon atoms, e.g. methyl chloroformate, is then added, again maintaining the temperature between −10° and 10° C. The reaction is completed by stirring at room temperature or refluxing the reaction for a period of one to 24 hours. The product Ia can can be isolated as described above.

For amidrazones, which contain a reactive group on the benzene ring, e.g. bromine, cyano or nitro, the butyllithium method of Equation B may not work well. In that case, the phosgene method described in Equation A can be used.

Compounds of this invention with Formula VI wherein n, m, Q, X, Y and Z are

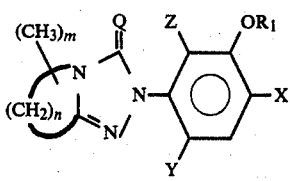

as determined in Formula I and V is $OR_1$, wherein
$R_1$ is alkyl of 1-6 optionally substituted with 1-3 fluorines, chlorines or bromines, cycloalkyl of 4-6, cycloalkylalkyl of 4-7, alkenyl of 3-6 optionally substituted with 1-3 fluorines, chlorines or bromines, alkynyl of 3-6, $-CHR_7R_8$ or

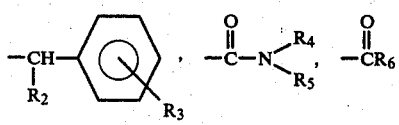

$R_2$ is hydrogen or methyl;
$R_3$ is hydrogen, chlorine, bromine, methyl or methoxy;
$R_4$ is alkyl of 1-4;
$R_5$ is methyl or methoxy;
$R_6$ is alkyl of 1-4 or alkoxy of 1-4
$R_7$ is hydrogen or alkyl of 1-4;
$R_8$ is $CO_2R_9$, CN,

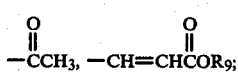

and
$R_9$ is hydrogen or alkyl of 1-4 carbons
are most readily prepared as shown in Equation C.

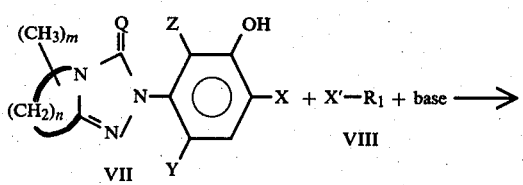

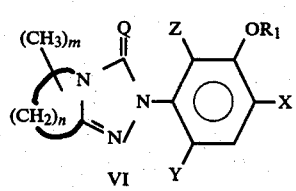

The phenol VII is combined with an appropriate halide VIII wherein $R_1$ has the meaning defined for compounds of Formula VI, X' is halogen, e.g., bromide or iodide and an equivalent amount of a suitable base, e.g., potassium carbonate, sodium hydroxide, sodium hydride, etc., in a solvent, e.g., acetonitrile, acetone, dimethyl formamide, etc. Addition of an alkali metal iodide, e.g., sodium iodide may facilitate the reaction. The reaction mixture is heated to reflux for a period of several hours, e.g., 1-24 hours. The crude product is obtained by pouring the reaction mixture into water. The product is extracted into a solvent, e.g. methylene chloride. The solution of the product is dried with a drying agent, e.g. anhydrous sodium sulfate and the solvent is then removed by evaporation on a rotary evaporator. The crude product thus obtained may be further purified by standard techniques, e.g. chromatography or crystallization.

The phenols VII of Equation C (or agriculturally suitable salts, e.g. sodium, potassium, lithium, triethylammonium, etc.) are novel compounds and active herbicides. Phenols of Formula VII are prepared from the corresponding amidrazones (Formula II wherein V is OH) as described in Equation A. Additionally phenols of Formula X (Q is oxygen in Formula VI)

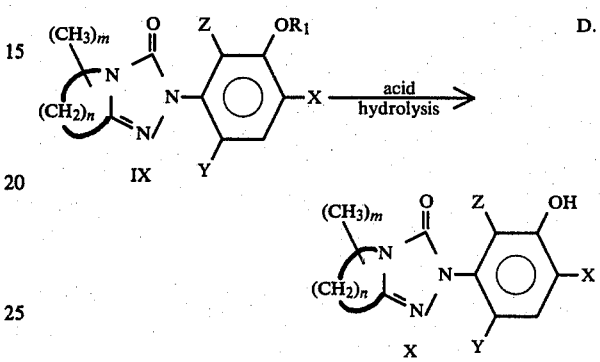

may be prepared by acid cleavage of a compound of Formula IX (wherein $R_1$ is alkyl of 1-6) as shown in Equation D. Suitable acids include concentrated sulfuric and concentrated hydrobromic.

Carboxylic acids of Formula XI, prepared as described in Equation C wherein

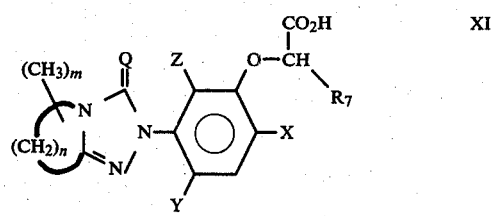

n, m, Q, X, Y, Z and $R_7$ are as defined in Formula I, are more readily prepared by acid or basic hydrolysis of related esters of Formula XII wherein $R_9$ is alkyl of 1-4 carbons

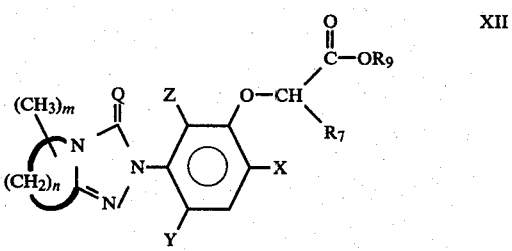

When carboxylic acids XI are reacted with thionyl chloride, following conditions well known in the literature for converting a carboxylic acid to a carboxylic acid chloride, compounds of Formula XIII are produced

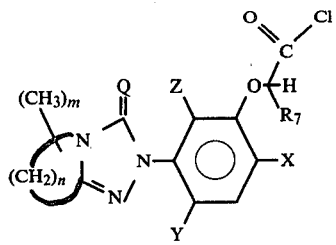

Reaction of compounds XIII with an amine XIV,

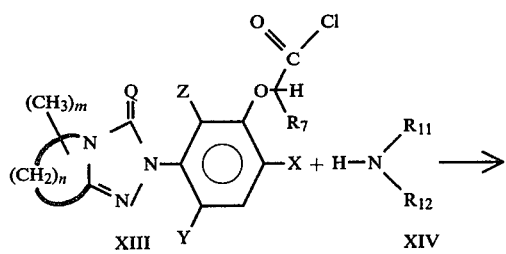

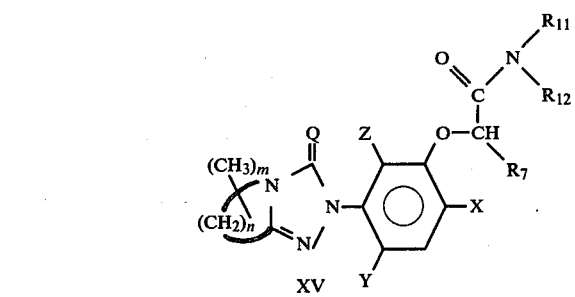

wherein $R_{11}$ and $R_{12}$ are as defined for compounds of Formula I, according to equation E using conditions well known in the literature for converting acid chlorides to amides leads to the carboxylic acid amides of Formula XV.

Compounds of this invention with Formula XVI wherein n, m, Q, X, Y, Z and $R_7$ are as defined in Formula I may be prepared by direct reduction of carboxylic acid esters XII with a suitable reducing agent, e.g. lithium borohydride in an appropriate solvent, e.g. tetrahydrofuran.

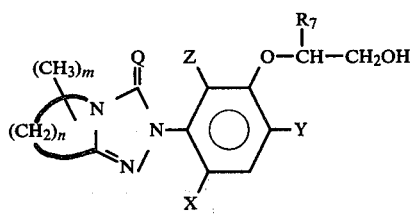

Treatment of the alcohols XVI with the appropriate anhydride XVII leads to

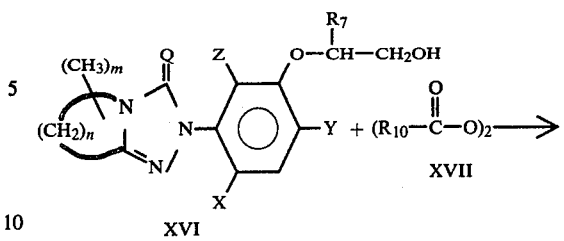

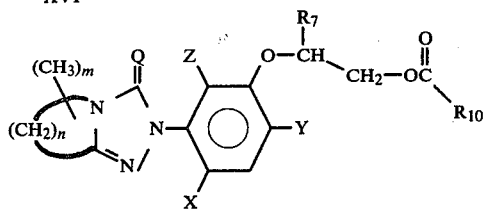

formation of ester XVIII of this invention wherein $R_{10}$ is as defined in Formula I (equation F).

Reaction of the phenols VII according to Equation G with the appropriate isocyanates.

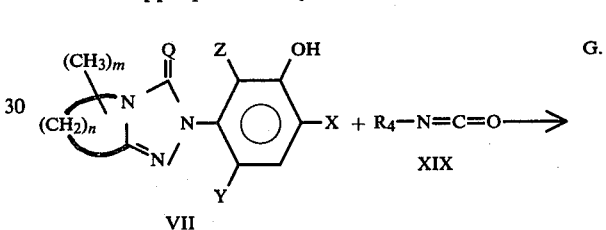

XIX wherein $R_4$ is alkyl of 1–4 carbons leads to formation of XX wherein $R_4$ is defined in Formula I.

The following examples further illustrate the preparation of the compounds of this invention. Unless otherwise designated all parts are by weight and all temperatures are °C.

EXAMPLE 1

Preparation of
2-(2,4-dichlorophenyl)-5,6,7,8-tetrahydro-1,2,4-triazolo[4,3-A]-pyridin-3(2H)-one 9.0 Parts of the hydrochloride salt of the 2,4-dichlorophenylhydrazone of 2-piperidone, prepared by methods similar to those described in German Offenlegungsschrift No. 2,235,113 and German Offenlegungsschrift No. 2,235,177, were combined with 200 parts of dry tetrahydrofuran and cooled to −10° C. under an atmosphere of nitrogen. To this solution, 37.2 parts of a solution of 1.6 m n-butyllithium (d=0.68) in hexane were added dropwise while maintaining the temperature of the reaction between −10° and 10° C. The reaction mixture was stirred for about 15 minutes following the addition of n-butyllithium. Then, 3.0 parts of methyl chloroformate were added dropwise while maintaining the temperature between −10° and 10° C. After addition of the chloroformate was completed, the reaction was allowed to warm to room temperature without cooling. It was then stirred for 30 minutes. The crude reaction mixture was poured into 500 parts of water. The aqueous solution was extracted 3 times with 200 parts of methylene chloride. The crude extracts were combined and dried over anhydrous sodium sulfate and then filtered. The solvent was removed from the filtrate by evaporation under a reduced pressure of 50–300 mm on a rotary evaporator. The crude product was purified by dry column chromatography over alumina and 5.4 parts of product were obtained as an oil which solidified after standing for 3 days (m.p. 100°–104° C.).

Using a procedure analogous to Example 1, with the appropriate amidrazones and methyl chloroformate, the following compounds of Formula I (wherein Q is oxygen) can be prepared (unless otherwise specified "Properties" designates melting point in °C.).

| n | Y | X | V | Z | m | Physical Properties |
|---|---|---|---|---|---|---|
| 4 | H | $CH_3$ | H | H | 0 | Wax-NMR($CDCl_3$) ($\delta$) 2.0 (m, 4H), 2.5 (s, 3H), 2.5 (m, 2H), 3.9 (m, 2H), 7.9 (A, A', B, B', 4H) |
| 4 | Cl | Cl | Cl | H | 0 | Oil-NMR($CDCl_3$) ($\delta$) 2.1 (m, 4H), 2.9 (m, 2H), 3.9 (m, 4H), 7.95 (s, 1H), 8.02 (s, 1H) |
| 4 | $CH_3$ | Cl | H | H | 0 | 117°–118° |
| 4 | F | Cl | H | H | 0 | 134°–137° |
| 4 | H | Cl | H | H | 0 | 120°–122° |
| 4 | H | $OCH_3$ | H | H | 0 | 110°–113° |
| 4 | F | F | H | F | 0 | 116°–118° |
| 4 | Cl | $CH_3$ | H | H | 0 | 91°–92° |
| 4 | Cl | Cl | H | Cl | 0 | Oil-NMR($CDCl_3$) ($\delta$) 2.0 (m, 4H), 2.8 (m, 2H) 3.8 (m, 2H), 7.3 (s, 2H) |
| 4 | Cl | Cl | F | H | 0 | |
| 4 | Cl | Cl | $CH_3$ | H | 0 | |
| 4 | Cl | Cl | $CH_3$ | H | 0 | |
| 4 | Cl | Cl | $CH_3-CH_2-CH_2-$ | H | 0 | |
| 4 | Cl | Cl | $-CH-(CH_3)_2$ | H | 0 | |
| 4 | Cl | Cl | $-CH-(CH_3)CH_2CH_3$ | H | 0 | |
| 4 | $CH_3$ | $CH_3$ | $CH_3$ | H | 0 | Oil-IR bands: 1725 $cm^{-1}$, 1600 $cm^{-1}$ |
| 3 | Cl | Cl | $OCH_3$ | H | 0 | Oil-NMR($CDCl_3$) ($\delta$) 2.9 (n, 4H), 4.0 (m, 5H) 7.4 (s, 1H), 7.9 (s, 1H) |
| 3 | Cl | Cl | $OCH_2CH_3$ | H | 0 | |
| 3 | Cl | Cl | $OCH(CH_3)_2$ | H | 0 | Oil-NMR($CDCl_3$) ($\delta$) 1.4 (d, 6H), 3.0 (m, 4H) (t, 2H) 4.6 (m, 1H), 7.3 (s, 1H) (s, 1H) |
| 3 | Cl | Cl | H | H | 0 | Oil-IR bands: 1720 $cm^{-1}$ 1620 $cm^{-1}$, 865 $cm^{-1}$, 830 $cm^{-1}$ |
| 5 | Cl | Cl | $OCH_3$ | H | 0 | 100°–102° |
| 5 | Cl | Cl | $OCH_2CH_3$ | H | 0 | |
| 5 | Cl | Cl | $OCH(CH_3)_2$ | H | 0 | Oil-IR bands: 1690 $cm^{-1}$, 1240 $cm^{-1}$, 1120 $cm^{-1}$ |
| 5 | Cl | Cl | $O(CH_2)_2CH_3$ | H | 0 | |
| 5 | Cl | Cl | H | H | 0 | 123°–126° |
| 5 | Cl | Cl | Cl | H | 0 | |
| 5 | F | Cl | H | H | 0 | 125°–128° |
| 5 | H | F | H | H | 0 | 72°–77° |

| n | Y | X | V | Z | m | Physical Properties |
|---|---|---|---|---|---|---|
| 4 | Cl | Cl | $OCH_3$ | H | 5-$CH_3$ | |
| 4 | Cl | Cl | $OCH(CH_3)_2$ | H | 5-$CH_3$ | |
| 4 | Cl | Cl | $OCH(CH_3)_2$ | H | 6-$CH_3$ | |
| 4 | Cl | Cl | $OCH_2CH_3$ | H | 6-$CH_3$ | |
| 4 | Cl | Cl | $OCH_3$ | H | 6-$CH_3$ | |
| 4 | Cl | Cl | $OCH_3$ | H | 7-$CH_3$ | Oil-IR bands: 1680 $cm^{-1}$, 1515 $cm^{-1}$ |
| 4 | Cl | Cl | H | H | 7-$CH_3$ | 98°–101° |

-continued

| n | Y | X | V | Z | | Physical Properties |
|---|---|---|---|---|---|---|
| 4 | Cl | Cl | OCH(CH₃)₂ | H | 7-CH₃ | |
| 4 | Cl | Cl | H | H | 8-CH₃ | Oil-IR bands: 1690 cm⁻¹, 1560 cm⁻¹ |
| 4 | Cl | Cl | OCH₃ | H | 8-CH₃ | Oil-IR bands: 1700 cm⁻¹, 1570 cm⁻¹ |
| 4 | Cl | Cl | O—CH(CH₃)₂ | H | 8-CH₃ | Oil-IR bands: 1700 cm⁻¹, 1580 cm⁻¹ |
| 4 | Cl | Cl | OCH₃ | H | 6-(CH₃)₂ | Oil-IR bands: 1710 cm⁻¹, 1580 cm⁻¹ |
| 4 | Cl | Cl | OCH(CH₃)₂ | H | 8-(CH₃)₂ | Oil-IR bands: 1710 cm⁻¹, 1570 cm⁻¹ |

EXAMPLE 2

Preparation of 2-(2,4-dichlorophenyl)-5,6,7,8-tetrahydro-1,2,4-triazolo[4,3-A]-pyridin-3-(2H)thione 4.5 Parts of the hydrochloride salt of the 2,4-dichlorophenylhydrazone of piperidone were combined with 100 parts of dry tetrahydrofuran and 4.6 parts of triethylamine. To this mixture were added 2.1 parts of thiophosgene. The reaction mixture was refluxed for 5 hours, after which the reaction mixture was filtered through 200 parts of activity grade II alumina (purchased from ICN Life Science, Cleveland, Ohio). The crude product was washed off the alumina with 500 parts of tetrahydrofuran. The filtrate was concentrated under a reduced pressure of 50-300 mm in a rotary evaporator. The crude product obtained was crystallized from a benzene-hexane mixture. 1.0 Part product with m.p. 118°-120° C. was obtained.

Using a procedure analogous to Example 2 with the appropriate amidrazone and thiophosgene, the following compounds of Formula I (wherein Q is sulfur) can be prepared.

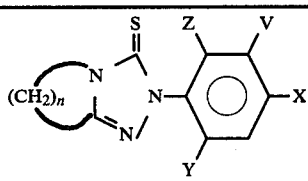

| n | Y | X | V | Z | Physical Properties |
|---|---|---|---|---|---|
| 4 | Cl | Cl | H | H | 118°-120° |
| 4 | H | NO₂ | H | H | |
| 4 | H | Cl | H | H | 171°-172° |
| 4 | Cl | Cl | OCH₃ | H | 136°-140° |
| 4 | Cl | Cl | OCH₂CH₃ | H | |
| 4 | Cl | Cl | OCH(CH₃)₂ | H | Oil-IR bands: 1580 cm⁻¹, 1240 cm⁻¹, 1120 cm⁻¹ |
| 4 | Cl | Br | OCH₂CH₃ | H | |
| 4 | F | Cl | H | H | 112°-116° |
| 5 | Cl | Cl | H | H | |
| 5 | H | NO₂ | H | H | Wax-IR bands: 1605 cm⁻¹, 855 cm⁻¹ |
| 5 | H | Cl | H | H | Oil-IR bands: 1610 cm⁻¹, 1030 cm⁻¹, 800 cm⁻¹ |
| 5 | Cl | Cl | OCH₃ | H | Oil-NMR (CDCl₃) (δ) 1.9 (m, 6H), 3.0 (m, 2H), 4.0 (s, 3H), 4.4 (m, 2H), 7.3 (s, 1H), 7.8 (s, 1H) |
| 5 | Cl | Cl | OCH₂CH₃ | H | |
| 5 | Cl | Cl | OCH(CH₃)₂ | H | Oil-NMR (CDCl₃) (δ) 1.5 (d, 6H), 2.0 (m, 6H), 3.0 (m, 2H), 4.1-5.0 (m, 3H), 7.5 (s, 1H), 8.0 (s, 1H) |
| 5 | Cl | Br | OCH₃ | H | |

Using a procedure analogous to Example 2 with the appropriate amidrazone and phosgene, the following compounds of Formula I (wherein Q is oxygen) can be prepared.

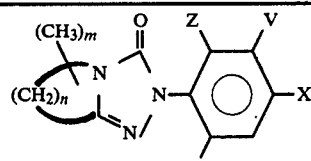

| n | Y | X | V | Z | m | Physical Properties |
|---|---|---|---|---|---|---|
| 4 | F | Br | H | H | 0 | |
| 4 | Cl | NO₂ | H | H | 0 | 204°-209° |
| 4 | H | CN | H | H | 0 | 164°-165° |
| 4 | Cl | Br | H | H | 0 | 136°-139° |
| 4 | Cl | NO₂ | OCH(CH₃)₂ | H | 0 | 141°-143° |
| 4 | Cl | Cl | OH | Br | 0 | 198°-201° |
| 4 | Cl | Cl | OCH₃ | Br | 0 | 152°-153° |
| 4 | Br | Cl | H | H | 0 | Oil-NMR (DMSO-d₆) (δ): 1.9 (m, 4H), 2.7 (m, 2H), 3.6 (m, 2H), 7.6 (m, 2H), 7.9 (m, 1H) |
| 4 | Cl | Cl | H | Br | 0 | |
| 4 | Cl | Cl | Br | H | 0 | Glass-NMR (CDCl₃) (δ): 2.0 (m, 4H), 2.8 (m, 2H), 3.8 (m, 2H), 7.9 (s, 1H), 8.1 (s, 1H) |
| 5 | Cl | NO₂ | H | O | 0 | 138°-141° |
| 5 | Cl | Cl | OH | O | 0 | |

EXAMPLE 3

Preparation of 2-(2,4-dichloro-5-hydroxyphenyl)-5,6,7,8-tetrahydro-1,2,4-triazolo[4,3-A]pyridin-3(2H)-one 42.8 Parts of 2-[2,4-dichloro-5-(1-methylethoxy)-phenyl]-5,6,7,8-tetrahydro-1,2,4-triazolo[4,3-A]pyridin-3(2H)-one prepared by a procedure analogous to Example 1 was combined with 45.6 gms of concentrated hydrobromic acid (48%). The mixture was heated to reflux for a period of four hours. 15 Parts of concentrated hydrobromic acid (48%) was added to the refluxing mixture and heating was continued for an additional 3 hours. The reaction mixture was allowed to cool to room temperature after which time it was poured into a liter of water. The crude product obtained by filtration was then added to 500 parts of water. The pH was adjusted to 12-14 with a 50% aqueous sodium hydroxide solution. The aqueous solution of product was then extracted three times with 250 parts of methylene chloride. The organic extracts were discarded. The aqueous layer was acidified with concentrated hydrochloric acid (38%) to pH 2-3. The product precipitated and was filtered. The product was further purified by crystallization from methanol-ethyl acetate mixture. The yield was 15.5 parts of product with m.p. 211°-212°.

EXAMPLE 4

Preparation of 2-[2,4-dichloro-5-(2-chloroethoxy)phenyl]-5,6,7,8-tetrahydro-1,2,4-triazolo[4,3-A]pyridin-3(2H)-one 3.0 Parts of 2-(2,4-dichloro-5-hydroxyphenyl)-5,6,7,8-tetrahydro-1,2,4-triazolo[4,3-A]pyridin-3(2H)-one prepared as described above in Example 3, 1.4 parts of 1-bromo-2-chloroethane, 1.5 parts of anhydrous potassium carbonate and 20 parts of dry acetonitrile were combined and refluxed for 6 hours followed by stirring for 72 hours at room temperature. The reaction mixture was poured into 200 parts of water. The aqueous suspension of the product was extracted three times with 200 parts of methylene chloride. The organic extracts of the product were dried with anhydrous sodium sulfate. The solvent was stripped from the product at reduced pressure on a rotary evaporator. The resulting dark oil was crystallized from ether yielding 0.2 parts of a light brown solid with m.p. 148°–150°.

Using a procedure analogous to Example 4 with the appropriate phenol of Formula VII and a halide of Formula VIII the following compounds of Formula I can be prepared.

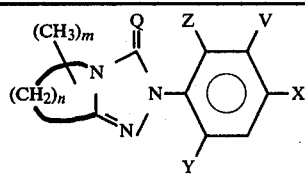

| n | Y | X | V | Z | m | Q | Physical Properties |
|---|---|---|---|---|---|---|---|
| 4 | Cl | Cl | OCH₃ | H | 0 | Oxygen | 160°–163° |
| 4 | Cl | Cl | O—CH₂CH₃ | H | 0 | " | 130°–132° |
| 4 | Cl | Cl | O—CH(CH₃)₂ | H | 0 | " | oil-IR bands: 1725 cm⁻¹ 1250 cm⁻¹, 1120 cm⁻¹ |
| 4 | Cl | Cl | O—(CH₂)₂CH₃ | H | 0 | " | 94°–96° |
| 4 | Cl | Cl | O—(CH₂)₃CH₃ | H | 0 | " | 114°–116° |
| 4 | Cl | Cl | O—CH₂—CH(CH₃)₂ | H | 0 | " | oil-NMR(CDCl₃) (δ) 1.1 (.1, 6H), 1.9(m, 5H), 2.8(m,2H), 3,8(m, 4H), 7.1 (S,1H), 7.5(S, 1H) |
| 4 | Cl | Cl | O—CH(CH₃)—CH₂CH₃ | H | 0 | " | oil-NMR (CDCl₃) (δ) .8–2.2(m-12H), 2.8(m,2H) 3.9(m,2H), 4.4(Q,1H), 7.1 (1H, S), 7.5(1H,S) |
| 4 | Cl | Cl | O—CH(CH₃)—CH₂—CH₂—CH₃ | H | 0 | " | oil-NMR (CDCl₃) (δ) .5–2.5(m.14H), 3.0(m,2H), 4.0(m,2H), 4,6(m,1H), 7.5 (S,1H), 8.0(S,1H) |
| 4 | Cl | Cl | O—CH—(CH₂CH₃)₂ | H | 0 | " | |
| 4 | Cl | Cl | O—CH(CH₃)(CH₂)₃CH₃ | H | 0 | " | |
| 4 | Cl | Cl | O-cyclopropyl | H | 0 | " | |
| 4 | Cl | Cl | O-cyclopentyl | H | 0 | " | oil-IR bands: 1680 cm⁻¹, 1560 cm⁻¹ |
| 4 | Cl | Cl | O-cyclohexyl | H | 0 | " | oil-IR bands: 1680 cm⁻¹, 1560 cm⁻¹ |
| 4 | Cl | Cl | O—CH₂-cyclopropyl | H | 0 | " | 116°–119° |
| 4 | Cl | Cl | O—CH₂-cyclobutyl | H | 0 | " | |
| 4 | Cl | Cl | O—CH₂-cyclopentyl | H | 0 | " | |
| 4 | Cl | Cl | O—CH₂-cyclohexyl | H | 0 | " | |
| 4 | Cl | Cl | O—CH₂—CH=CH₂ | H | 0 | " | oil-NMR(CDCl₃-S) 1.9(m,4H), 1.7(m,2H), |

-continued

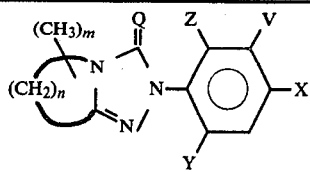

| n | Y | X | V | Z | m | Q | Physical Properties |
|---|---|---|---|---|---|---|---|
|   |   |   |   |   |   |   | 2.7(m,2H), 4.6(m,2H), 5.2–6.5(m,3H), 7.1(S,1H), 7.5(S,1H) |
| 4 | Cl | Cl | O—CH(CH₃)—CH=CH₂ | H | 0 | " |  |
| 4 | Cl | Cl | O—CH(CH₃)—CH=CH—CH₃ | H | 0 | " |  |
| 4 | Cl | Cl | O—CH(CH₃)—CH=CH—CH₂CH₃ | H | 0 | " |  |
| 4 | Cl | Cl | O—CH₂—C≡C—H | H | 0 | " | 167°–169° |
| 4 | Cl | Cl | O—CH(CH₃)—C≡C—CH₂CH₃ | H | 0 | " |  |
| 4 | Cl | Cl | O—CH(CH₃)—C≡C—H | H | 0 | " |  |
| 4 | Cl | Cl | O—CH(CH₃)—C≡C—CH₃ | H | 0 | " |  |
| 4 | Cl | Cl | O—CH₂—C₆H₅ | H | 0 | " |  |
| 4 | Cl | Cl | O—CH(CH₃)—C₆H₅ | H | 0 | " | NMR (CDCl₃) (δ) 2.0 (m,4H), 2.9 (m,2H), 3.9 (m,2H), 5.2 (S,2H), 7.5–8.0 (m,7H) |
| 4 | Cl | Cl | O—CH(CH₃)—C₆H₄—OCH₃ | H | 0 | " |  |
| 4 | Cl | Cl | O—CH(CH₃)—C₆H₄—Cl (o) | H | 0 | " |  |
| 4 | Cl | Cl | O—CH(CH₃)—C₆H₄—Br (o) | H | 0 | " |  |
| 4 | Cl | Cl | O—CH(CH₃)—C₆H₄—CH₃ (m) | H | 0 | " |  |
| 4 | Cl | Cl | O—C(=O)—N(CH₃)₂ | H | 0 | " |  |
| 4 | Cl | Cl | O—C(=O)—N(CH₃)(CH₂CH₃) | H | 0 | " |  |
| 4 | Cl | Cl | O—C(=O)—N(CH₃)(CH₂CH₂CH₃) | H | 0 | " |  |
| 4 | Cl | Cl | O—C(=O)—N(CH₃)(CH₂CH₂CH₂CH₃) | H | 0 | " |  |

-continued

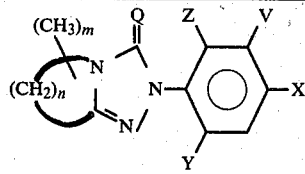

| n | Y | X | V | Z | m | Q | Physical Properties |
|---|---|---|---|---|---|---|---|
| 4 | Cl | Cl | O−C(=O)−N(CH₃)(OCH₃) | H | 0 | " | |
| 4 | Cl | Cl | O−C(=O)−CH₃ | H | 0 | " | oil (NMR) (CDCl₃) (δ) 2.0 (m,4H), 2.4(s,3H), 2.7 (m,2H), 3.8 (m,2H), 7.56 (s,1H), 7.8 (s, 1H) |
| 4 | Cl | Cl | O−C(=O)−CH₂−CH₃ | H | 0 | " | |
| 4 | Cl | Cl | O−C(=O)−CH(CH₃)₂ | H | 0 | " | |
| 4 | Cl | Cl | O−C(=O)−CH₂−CH(CH₂CH₃) | H | 0 | " | |
| 4 | Cl | Cl | O−C(=O)−OCH₃ | H | 0 | " | oil (NMR) (CDCl₃) (δ) 2.0 (m,4H), 2.9 (m,2H), 3.9 (m, 2H), 4.1 (s,3H), 7.9 (s,1H), 8.1 (s, 1H) |
| 4 | Cl | Cl | O−C(=O)−OCH₂CH₃ | H | 0 | " | |
| 4 | Cl | Cl | O−C(=O)−OCH(CH₃)₂ | H | 0 | " | |
| 4 | Cl | Cl | O−C(=O)−OCH(CH₃)CH₂CH₃ | H | 0 | " | 172°-174° |
| 4 | Cl | Cl | OCH₂CN | H | 0 | " | |
| 4 | Cl | Cl | OCH(CH₃)−CN | H | 0 | " | |
| 4 | Cl | Cl | O−CH₂−C(=O)−CH₃ | H | 0 | " | 62°-64° |
| 4 | Cl | Cl | O−CH(CH₃)−C(=O)−CH₃ | H | 0 | " | |
| 4 | Cl | Cl | O−CH₂−CH=CH−C(=O)−OCH₃ | H | 0 | " | Oil (IR; 1700 cm⁻¹, 1580 cm⁻¹) |
| 4 | Cl | Cl | O−CH(CH₃)−CH=CH−C(=O)−OCH₂CH₃ | H | 0 | " | |
| 4 | Cl | Cl | O−CH₂−CH=CH−C(=O)−O(CH₂)₃CH₃ | H | 0 | " | |
| 4 | F | Cl | OCH₃ | H | 0 | " | |
| 4 | F | Cl | O−CH(CH₃)₂ | H | 0 | " | |
| 4 | Cl | Br | OCH₃ | H | 0 | " | |
| 4 | Cl | Br | OCH₂CH₃ | H | 0 | " | |
| 4 | Cl | Br | OCH(CH₃)₂ | H | 0 | " | |
| 4 | Cl | Br | OCH₂−C≡CH | H | 0 | " | |
| 4 | Cl | Cl | O−CH(CH₃)−CH₂OCH₃ | H | 0 | " | |
| 4 | Cl | Cl | O−CH₂−CH₂−OCH₂CH₃ | H | 0 | " | oil-IR bands: 1700 cm⁻¹, 1590 cm⁻¹ |
| 4 | Cl | Cl | O−CH₂−CH₂−O(CH₂)₂CH₃ | H | 0 | " | |
| 4 | Cl | Cl | O−CH₂−CH₂−O(CH₂)₃CH₃ | H | 0 | " | |
| 4 | Cl | Cl | O−C(=O)−NHCH₂CH₃ | H | 0 | " | |
| 4 | Cl | Cl | O−C(=O)−NHCH₃ | H | 0 | Sulfur | |
| 4 | Cl | Cl | O−C(=O)−NH(CH₂)₂CH₃ | H | 0 | Oxygen | |
| 4 | Cl | Cl | O−C(=O)−NH−C(CH₃)₃ | H | 0 | " | 163°-165° |

-continued

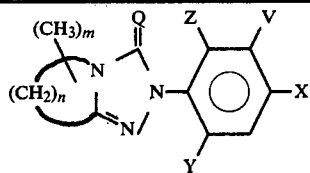

| n | Y | X | V | Z | m | Q | Physical Properties |
|---|---|---|---|---|---|---|---|
| 5 | Cl | Cl | O—C(=O)—NHCH$_3$ | H | 0 | " | |
| 5 | Cl | Cl | OCH$_2$—CH=CH$_2$ | H | 0 | " | |
| 5 | Cl | Cl | O—CH(CH$_3$)—CH=CH$_2$ | H | 0 | " | |
| 5 | Cl | Cl | OCH(CH$_3$)—C≡C—H | H | 0 | " | |
| 5 | Cl | Cl | OCH$_2$—C≡C—H | H | 0 | " | |
| 5 | Cl | Cl | OCH$_2$—C$_6$H$_5$ | H | 0 | " | |
| 5 | Cl | Cl | O—CH(CH$_3$)—C$_6$H$_5$ | H | 0 | " | |
| 5 | Cl | Cl | O—C(=O)—N(CH$_3$)$_2$ | H | 0 | " | |
| 5 | Cl | Cl | O—CH(CH$_3$)—CN | H | 0 | " | |
| 5 | Cl | Cl | OCH$_2$CH$_2$—Cl | H | 0 | " | |
| 4 | Cl | Cl | O—CH$_2$CF$_3$ | H | 0 | " | |
| 4 | Cl | Cl | O—CH$_2$F | H | 0 | " | |
| 4 | Cl | Cl | O(CH$_2$)$_3$Cl | H | 0 | " | |
| 4 | Cl | Cl | O(CH$_2$)$_4$Br | H | 0 | " | |
| 4 | Cl | Cl | O(CH$_2$)$_5$Br | H | 0 | " | |
| 4 | Cl | Cl | O(CH$_2$)$_6$—Cl | H | 0 | " | |
| 4 | Cl | Cl | O—CH$_2$—CH(Cl)—CH$_2$Cl | H | 0 | " | |
| 4 | Cl | Cl | —O—CH$_2$—CH=CH—Br | H | 0 | " | |
| 4 | Cl | Cl | O—CH$_2$—CH=CH—F | H | 0 | " | |
| 4 | Cl | Cl | O—CH$_2$—CCl=CHCl | H | 0 | " | |
| 4 | Cl | Cl | O—CH$_2$—CCl=C(Cl)$_2$ | H | 0 | " | Oil (NMR) (CDCl$_3$) (δ) mixture of cis/trans isomers; 2.0 (m,4H), 2.7 (m,2H), 3.7 (m,2H), 4.7–4.9 (2H), 6.5–6.7 (1H), 7.1 (s,1H), 7.5 (s,1H) |
| 4 | Cl | Cl | CH$_2$=CCl—CH(—O)—CH$_3$ | H | 0 | " | |
| 4 | Cl | Cl | —O—CH$_2$=CCl—CH(Cl)—CH$_2$—CH$_2$—Cl | H | 0 | " | |
| 4 | Cl | Cl | O—CH$_2$—CH=C(Cl)—CH$_2$—CH$_2$—CH$_3$ | H | 0 | " | |

EXAMPLE 5

Preparation of 2-[2,4-dichloro-5-(1-ethoxy-carbonylethoxy)-phenyl]-5,6,7,8-tetrahydro-1,2,4-triazolo[4,3-A]pyridin-3(2H)-one 20.1 Parts of 2-(2,4-dichloro-5-hydroxy phenyl)-5,6,7,8-tetrahydro-1,2,4-triazolo[4,3-A]pyridin-3(2H)-one prepared as described in Example 3, 12.1 parts of ethyl-2-bromopropionate, 9.3 parts of anhydrous potassium carbonate and 100 parts of dry acetonitrile were refluxed for 5 hours. The reaction was cooled and poured into 250 parts of H$_2$O. The aqueous suspension of product was extracted three times with 250 parts of methylene chloride and then the solution was dried with anhydrous sulfate. The solvent was removed on a rotary evaporator at reduced pressure. The glassy residue was crystallized from ethyl acetate-ether mixture. The yield was 16.0 parts of a light brown solid with m.p. 136°–138°.

Using a procedure analogous to Example 5 with a phenol of Formula VII and the appropriate α-halo ester of Formula VIII, the following compounds of Formula I can be prepared.

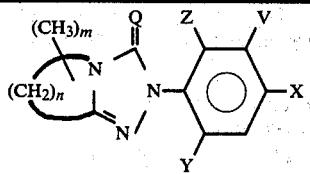

| n | Y | X | V | Z | m | Q | Physical Properties |
|---|---|---|---|---|---|---|---|
| 4 | Cl | Cl | O—CH$_2$—C(=O)—OCH$_3$ | H | 0 | Oxygen | 172–174 |
| 4 | Cl | Cl | O—CH(CH$_3$)—C(=O)—OCH$_3$ | H | 0 | Oxygen | |
| 4 | Cl | Cl | O—CH(CH$_3$)—C(=O)—OCH$_2$CH$_2$CH$_3$ | H | 0 | Oxygen | |
| 4 | Cl | Cl | O—CH(CH$_3$)—C(=O)—O(CH$_2$)$_3$CH$_3$ | H | 0 | Oxygen | |
| 5 | Cl | Cl | O—CH(CH$_3$)—C(=O)—OCH$_3$ | H | 0 | Oxygen | |
| 5 | Cl | Cl | O—CH(CH$_3$)—C(=O)—OCH$_2$CH$_3$ | H | 0 | Oxygen | |
| 4 | Cl | Cl | O—CH(CH$_2$CH$_3$)—C(=O)—OCH$_3$ | H | 0 | Oxygen | |
| 4 | Cl | Cl | O—CH((CH$_2$)$_2$CH$_3$)—C(=O)—OCH$_3$ | H | 0 | Oxygen | |
| 4 | Cl | Cl | O—CH((CH$_2$)$_3$CH$_3$)—C(=O)—OCH$_3$ | H | 0 | Oxygen | |

EXAMPLE 6

Preparation of 2[2,4-dichloro-5-(1-carboxy-ethoxy)-phenyl]-5,6,7,8-tetrahydro-1,2,4-triazolo[4,3-A]pyridine-3(2H)-one 10.8 Parts of 2-[2,4-dichloro-5-(1-ethoxy-carbonylethoxy)-phenyl]-5,6,7,8-tetrahydro-1,2,4-triazolo[4,3-A]pyridin-3(2H)-one, 20.6 parts of concentrated hydrochloric acid (38%) and 175 parts of dioxane were combined and heated to 80° for 30 hours. After cooling the solution was poured into 750 parts of water. The pH of the solution was raised to 8–9 by addition of solid sodium bicarbonate. The aqueous solution of the product was then extracted three times with 250 parts of methylene chloride. The organic extracts were discarded. The aqueous solution of the product was then acidified to pH 1 by addition at concentrated hydrochloric acid (38%). The aqueous solution of product was extracted three times with 250 parts of methylene chloride. The solution of product was dried with anhydrous sodium sulfate. The solvent was removed on a rotary evaporator at reduced pressure. The glassy residue was triturated with ether. 4.4 Parts of white solid with m.p. 183°–185° were obtained.

Using a procedure analogous to Example 6 with the appropriate ester of Formula XII the following compounds of Formula I can be prepared.

| n | Y | X | V | Z | m | Q | Physical Properties |
|---|---|---|---|---|---|---|---|
| 4 | Cl | Cl | O—CH$_2$—CO$_2$H | H | 0 | oxygen | Oil-IR bands: 3400–2200 cm$^{-1}$, (br), 1750–1600 cm$^{-1}$ (br), 1560 cm$^{-1}$ |
| 4 | Cl | Br | O—CH(CH$_3$)—CO$_2$H | H | 0 | oxygen | |
| 4 | F | Cl | O—CH(CH$_3$)—CO$_2$H | H | 0 | oxygen | |
| 5 | Cl | Cl | O—CH(CH$_3$)—CO$_2$H | H | 0 | oxygen | |

EXAMPLE 7

Preparation of 2-[2,4-dichloro-5-(1-N-methoxy-N-methyl carbamoyl-ethoxy)-phenyl]-5,6,7,8-tetrahydro-1,2,4-triazolo[4,3-A]pyridin-3(2H)-one

(a) Preparation of 2-[2,4-dichloro-5-(1-chlorocarbonylethoxy)-phenyl]-5,6,7,8-tetrahydro-1,2,4triazolo[4,3-A]pyridin-3(2H)-one 3.7 Parts of 2-[2,4-dichloro-5-(1-carboxy-ethoxy)-phenyl]-5,6,7,8-tetrahydro-1,2,4-triazolo[4,3-A]pyridin-3(2H)-one, 15 parts of chloroform and 1.2 parts of thionyl chloride were combined and refluxed for 3 hours. The reaction was stirred for an additional 12 hours at room temperature. Solvent and excess thionyl chloride were removed from the product by evaporation on a rotary evaporator at reduced pressure. 4.0 Parts of crude product were obtained and used in the next step without further purification.

(b) Preparation of 2-[2,4-dichloro-5-(1-N-methoxy-N-methyl carbamoyl-ethoxy)-phenyl]-5,6,7,8-tetrahydro-1,2,4-triazolo[4,3-A]pyridin-3(2H)-one 4.0 Parts of the crude acid chloride from Example 7a were dissolved in 50 parts of toluene containing 2.2 parts of triethylamine and 1.3 parts of N-methoxy-N-methylamine. The reaction mixture was stirred for 3 hours at room temperature. 50 Parts of water were added to the mixture and the reaction was stirred for 10 more minutes. The organic phase was separated and it was then washed twice with 25 parts of saturated sodium bicarbonate solution and once with 25 parts of water. The organic layer was dried with saturated sodium sulfate. The solvent was removed on a rotary evaporator at reduced pressure yielding 1.4 parts of a glassy solid with the following NMR spectrum:

$CDCl_3$ ($\delta$) 1.7 (d, 3H), 2.0 (m, 4H), 2.7 (m, 2H), 3.2 ($\delta$, 3H), 3.7 (m, 5H), 5.2 (q, 1H), 7.1 (s, 1H), 7.5 (s, 1H).

Using a procedure analogous to Example 7b with the appropriate acid chloride of Formula XIII prepared as described in Example 7a and appropriate amine of Formula XIV the following compounds of Formula I can be prepared.

| n | Y | X | V | Z | m | Q | Physical Properties |
|---|---|---|---|---|---|---|---|
| 4 | Cl | Cl | OCH$_2$—C(=O)—NH$_2$ | H | 0 | Oxygen | 205°-207° |
| 4 | Cl | Cl | OCH(CH$_3$)—C(=O)—NHCH$_3$ | H | 0 | Oxygen | |
| 4 | Cl | Cl | OCH(CH$_3$)—C(=O)—N(CH$_3$)$_2$ | H | 0 | Oxygen | |
| 4 | Cl | Cl | O—CH(CH$_3$)—C(=O)—N(CH$_3$)(CH$_2$CH$_3$) | H | 0 | Oxygen | |
| 4 | Cl | Cl | OCH(CH$_3$)—C(=O)—N(CH$_2$CH$_3$)((CH$_2$)$_2$CH$_3$) | H | 0 | Oxygen | |
| 4 | Cl | Cl | OCH(CH$_3$)—C(=O)—N(CH$_3$)((CH$_2$)$_3$CH$_3$) | H | 0 | Oxygen | |
| 5 | Cl | Cl | OCH(CH$_3$)—C(=O)—N(CH$_3$)(OCH$_2$CH$_3$) | H | 0 | Oxygen | |
| 5 | Cl | Cl | O—CH(CH$_3$)—C(=O)—N(CH$_3$)$_2$ | H | 0 | Oxygen | |
| 5 | Cl | Cl | O—CH(CH$_3$)—C(=O)—N(CH$_3$)(OCH$_3$) | H | 0 | Oxygen | |
| 5 | Cl | Cl | O—CH(CH$_3$)—C(=O)—NH—CH$_2$—CH$_2$=CH$_2$ | H | 0 | Oxygen | |
| 5 | Cl | Cl | O—CH(CH$_3$)—C(=O)—NH—CH(CH$_3$)—CH=CH$_2$ | H | 0 | Oxygen | |
| 5 | Cl | Cl | O—CH(CH$_3$)—C(=O)—NH$_2$ | H | 0 | Oxygen | |
| 4 | Cl | Cl | O—CH(CH$_3$)—C(=O)—N(CH$_3$)$_2$ | H | 0 | Sulfur | |

EXAMPLE 8

Preparation of
2-(2,4-dichloro-5-hydroxyphenyl)-5,6,7,8-tetrahydro-1,2,4-triazolo[4,3-A]pyridin-3(2H)-one, methyl carbamate A mixture of 25 parts of methylene chloride, 1.1 parts of methyl isocyanate, 3.0 parts of 2-(2,4-dichloro-5-hydroxy phenyl)-5,6,7,8-tetrahydro-1,2,4-triazolo[4,3-A] pyridin-3(2H)-one and 0.05 part of 1,4-diazobicyclo [2.2.2] octane was refluxed 4 hours. The solvent was removed on a rotary evaporator at reduced pressure and the crude product obtained was crystallized from acetonitrile yielding 2.5 parts solid product with m.p. 167°-170°.

Using a procedure analogous to Example 8 with a phenol of Formula VII and the appropriate isocyanate the following compounds of Formula I can be prepared.

| n | Y  | X  | V                                  | Z | m | Q      |
|---|----|----|------------------------------------|---|---|--------|
| 4 | Cl | Cl | O—CNHCH$_2$CH$_3$ (C=O)            | H | 0 | Oxygen |
| 4 | Cl | Cl | O—C(=O)—NH(CH$_2$)$_2$CH$_3$       | H | 0 | Sulfur |
| 5 | Cl | Cl | O—C(=O)—NH(CH$_2$)$_3$CH$_3$       | H | 0 | Oxygen |
| 5 | Cl | Cl | O—C(=O)—NHCH$_3$                   | H | 0 | Oxygen |

EXAMPLE 9

Preparation of
2-[2,4-dichloro-5-(1-hydroxymethyl-ethoxy)-phenyl]-5,6,7,8-tetrahydro-1,2,4-triazolo[4,3-A]pyridin-3(2H)-one 4.0 Parts of 2-[2,4-dichloro-5-(1-ethoxy-carbonylethoxy)-phenyl]-5,6,7,8-tetrahydro-1,2,4-triazolo[4,3-A] pyridin-3(2H)-one prepared as described in Example 5 in 75 parts of tetrahydrofuran was treated with 0.3 part of sodium borohydride and 0.3 part of lithium chloride. The reaction was heated to 40° for 6 hours. After this period 0.6 part of sodium borohydride and 0.5 parts of lithium chloride were added and the reaction was then stirred for 12 hours at room temperature. The reaction was heated to reflux and an additional 3.0 parts of sodium borohydride and 2.8 parts of lithium chloride were added in small portions over 48 hours. The mixture was cooled and added slowly to 100 parts of water whereby some foaming occurred. The product was extracted three times with 200 parts of ether. The ether was then extracted twice with 100 parts of water. The ether layer was dried with sodium sulfate. The ether was stripped on a rotary evaporator at reduced pressure. The residue was triturated with methylene chloride yielding 0.35 part of a tan solid with m.p. 54°-57°.

Using a procedure analogous to Example 9 with the appropriate carboxylic acid of Formula XI the following compounds of Formula I can be prepared.

| n | Y  | X  | V                          | Z | m | Q      | Physical Properties |
|---|----|----|----------------------------|---|---|--------|---------------------|
| 4 | Cl | Cl | OCH$_2$CH$_2$OH            | H | 0 | oxygen | Oil-NMR (CDCl$_3$) (δ) 2.0 (m, 4H), 2.8 (m, 3H), 3.5–4.5 (m, 6H), 7.4 (s, 1H), 7.8 (s, 1H) |
| 5 | Cl | Cl | O—CH(CH$_3$)—CH$_2$OH      | H | 0 | oxygen |                     |
| 5 | Cl | Cl | O—CH$_2$CH$_2$OH           | H | 0 | oxygen |                     |

EXAMPLE 10

Preparation of
2-[[5-(2-acetyloxy)ethoxy]-2,4-dichlorophenyl]-5,6,7,8-tetrahydro-1,2,4-triazolo[4,3-A]pyridin-3(2H)-one 3.8 Parts of 2-[2,4-dichloro-5-(2-hydroxy-ethoxy)phenyl]-5,6,7,8-tetrahydro-1,2,4-triazolo[4,3-A]pyridin-3(2H)-one prepared by a procedure analogous to Example 9 was combined with 2.2 parts of anhydrous sodium acetate, and 2.8 parts of acetic anhydride in 15 parts of toluene. The reaction mixture was warmed to 80° for 3 hours and then cooled to room temperature. The reaction mixture was poured into water. The organic phase was taken up in 200 parts of methylene chloride and dried with anhydrous sodium sulfate. The solvent was removed on a rotary evaporator at reduced pressure. 3.0 Parts of oil was obtained.

NMR-CDCl$_3$ (δ): 1.8-2.4 (m, 7H), 2.8 (m, 2H), 3.9 (m, 2H), 4.3–4.8 (m, 4H), 7.4 (s, 1H), 7.9 (s, 1H)

Using a procedure analogous to Example 10 with the appropriate alcohol of Formula XVI and anhydride XVII the following compounds of Formula I can be prepared.

| n | Y  | X  | V                                              | Z | m | Q      |
|---|----|----|------------------------------------------------|---|---|--------|
| 4 | Cl | Cl | O—CH(CH$_3$)—CH$_2$—O—C(=O)—CH$_3$             | H | O | oxygen |
| 5 | Cl | Cl | O—CH$_2$—CH$_2$—O—C(=O)—CH$_2$CH$_3$           | H | O | oxygen |
| 4 | Cl | Cl | O—CH$_2$CH$_2$—O—C(=O)—(CH$_2$)$_2$CH$_3$      | H | O | oxygen |

Formulations

Useful formulations of the compounds of Formula I include dusts, granules, pellets, solutions, suspensions, emulsions, wettable powders, emulsifiable concentrates and the like. Many of these formulations can be applied directly. Sprayable formulations can be extended in suitable media and used at spray volumes of from a few liters to several hundred liters per hectare. High strength formulations are used primarily for preparing more dilute field strength formulations. The formulations, broadly, consist essentially of about 0.05% to 99% by weight of active ingredient(s) and at least one of (a) about 0.1% to 20% surfactant(s) and (b) about 1% to 99.95% solid or liquid diluent(s). More specifically, they will usually consist essentially of these ingredients in the following approximate proportions:

|  | Percent by Weight | | |
|---|---|---|---|
|  | Active Ingredient | Diluent(s) | Surfactant(s) |
| Wettable Powders | 5–90 | 1–94 | 1–10 |
| Oil Suspensions, Emulsions, Solutions (including Emulsifiable Concentrates) | 5–50 | 40–95 | 0–15 |
| Aqueous Suspensions | 5–50 | 40–94 | 1–20 |
| Dusts | 0.05–25 | 70–99.95 | 0–5 |
| Granules and Pellets | 0.05–95 | 1–99.95 | 0–15 |
| High Strength Compositions | 90–99 | 0–10 | 0–2 |

Any compound of Formula I can be made in these formulations.

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook on Insecticide Dust Diluents and Carriers", 2nd. Edn., Dorland Books, Caldwell, N.J. Suitable diluents include finely divided or granular solids classified as attapulgites, botanicals, calcites, diatomites, dolomites, gypsum, kaolinites, limestones, mica, montmorillonoids, phosphates, pyrophyllites, sulfur, sand, talcs, tripolites, vermiculite, and synthetics such as precipitated, hydrated silicon dioxide, precipitated, hydrated calcium silicate, precipitated calcium carbonate and synthetic organics. The more absorptive diluents are preferred for wettable powders and the denser ones for dusts. Typical liquid diluents and solvents are described in Marsden, "Solvents Guide", 2nd. Edn., Interscience, New York, 1950. Solubility under 0.1% is preferred for suspension concentrates; solution concentrates are preferably stable against phase separation at 0° C. "McCutcheon's Detergents and Emulsifiers 1975 Annual", MC Publ. Corp., Ridgewood, New Jersey, as well as Sisely and Wood, "Encyclopedia of Surface Active Agents", Chemical Publ. Col, New York, 1964, list surfactants and recommended uses. All formulations can contain minor amounts of additives to reduce foaming, caking, corrosion, microbiological growth, etc., or to mark visually the area that has been treated.

Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084).

Granules may be made in several ways. For example, the active ingredient may be sprayed onto preformed granular carriers. Suitable preformed granular carriers include those suitable diluents listed earlier having a particle size range from USS Sieve No. 200 (74 microns) to USS Sieve No. 10 (2000 microns). The preferred particle size is from USS Sieve No. 140 (105 microns) to USS Sieve No. 20 (840 microns). Depending upon the nature of the carrier, the active ingredient may remain on the surface of the carrier or be absorbed into the carrier. Usually when the active ingredient remains on the surface of the carrier, a binding agent is used to hold the active ingredient on the surface. The binding agent should bind the active ingredient to the surface well enough so that no more than 10% of the active ingredient is removed during normal shipping and handling operations. Suitable binding agents include materials which are at least partially soluble in any liquid used in the manufacture of the granules and which adhere to the granular surface. Water-soluble binders are preferred. Suitable binders include, but are not limited to, water-soluble polymers such as polyvinylalcohols, polyvinylpyrrolidones, polyoxyethylenes. Other suitable binders include, ligninsulfonates, starches, sugars, and certain surface active agents listed in "McCutcheons' Detergents and Emulsifiers 1975 Annual", MC Publ. Corp., Ridgewood, New Jersey.

The active ingredient may be sprayed onto the granules as a solution in a suitable solvent, which may or may not be removed from the formulation. If the active ingredient is a liquid, it may be sprayed onto or mixed with the carrier directly. If it is a solid, it may be melted and applied directly as a liquid. If very low strength granules are desired, the active ingredient may be atomized onto the carrier. Granules may also be prepared by agglomeration techniques. For example, the active ingredient and a finely divided solid diluent may be mixed and agglomerated by techniques known in the art, such as by spraying with a liquid in a fluidized bed or pan granulator. The active ingredient and diluent may also be mixed with other formulation ingredients and pelletized. The pellets may then be crushed to a desired granular size. Pellets may be made by agglomeration techniques. See J. E. Browning, "Agglomeration", Chemical Engineering, Dec. 4, 1967, pp. 147ff. and "Perry's Chemical Engineer's Handbook", 4th Edn., McGraw-Hill, N.Y., 1963, pp. 8-59ff.

For further information regarding the art of formulation, see for example:

H. M. Loux, U.S. Pat. No. 3,235,361, Feb. 15, 1966, Col. 6, Line 16 through Col. 7, Line 19 and Examples 10 through 41.

R. W. Luckenbaugh, U.S. Pat. No. 3,309,192, March 14, 1967, Col. 5, Line 43 through Col. 7, Line 62, and Ex. 8, 12, 15, 39, 41, 52, 53, 58, 132, 138-140, 162-164, 166, 167, 169-182.

H. Gysin and E. Knusli, U.S. Pat. No. 2,891,855, June 23, 1959, Col. 3, Line 66 through Col. 5, Line 17 and Examples 1-4.

G. C. Klingman, "Weed Control as a Science", John Wiley & Sons, Inc., New York, 1961 pp. 81-96.

J. D. Fryer and S. A. Evans, "Weed Control Handbook", 5th Edn. Blackwell Scientific Publications, Oxford, 1968, pp. 101-103.

EXAMPLE 11

| Wettable Powder | |
|---|---|
| 2-(2,4-dichloro-5-ethoxyphenyl)-5,6,7,8-tetrahydro-1,2,4-triazolo-[4,3-A]-pyridin-3(2H)-one | 25% |
| Sodium ligninsulfonate | 2% |
| Sodium alkylnaphthalene sulfonate | 2% |
| Synthetic amorphous silica | 3% |
| Kaolinite | 68% |

The ingredients are blended thoroughly, ground in an air mill to produce an average particle size under 15 microns, reblended and sifted through a U.S.S. No. 50 sieve (0.3 mm opening) before packaging.

EXAMPLE 12

| Solution | |
|---|---|
| 2-[2,4-dichloro-5-(1-methylethoxy)-phenyl]-5,6,7,8-tetrahydro-1,2,4-triazolo[4,3-A]-pyridin-3(2H)-one | 20% |
| Dimethylformamide | 80% |

The ingredients are combined and stirred to produce a solution, which can be used for low-volume applications.

EXAMPLE 13

| Extruded Pellet | |
|---|---|
| 2-(2,4-dichloro-5-ethoxyphenyl)-5,6,7,8-tetrahydro-1,2,4-triazolo-[4,3-A]-pyridin-3(2H)-one | 1% |
| Anhydrous sodium sulfate | 10% |
| Crude Calcium ligninsulfonate | 5% |
| Sodium alkylnaphthalenesulfonate | 1% |
| Polyoxyethylene (4 × $10^6$ average molecular weight) | 1% |
| Calcium/magnesium bentonite | 82% |

The ingredients are blended, hammer milled and then moistened with about 12% water. The mixture is extruded as cylinders about 3 mm diameter which are cut to produce pellets about 3 mm long. These may be used directly after drying, or the dried pellets may be crushed to pass a U.S.S. No. 20 sieve (0.84 mm openings). The granules held on a U.S.S. No. 40 sieve (0.42 mm openings) may be packaged for use and the fines recycled.

EXAMPLE 14

| Emulsifiable Concentrate | |
|---|---|
| 2-[2,4-dichloro-5-(1-methoxyethoxy)-phenyl]-2,5,6,7,8,9-hexahydro-3H-1,2,4-triazolo[4,3-A]-azepin-3-one | 25% |
| Blend of oil soluble sulfonates and polyoxyethylene ethers | 4% |
| Xylene | 71% |

The ingredients are combined and stirred until solution is complete. A fine screen filter is included in packaging operation to insure the absence of any extraneous undissolved material in the product.

EXAMPLE 15

| Aqueous Suspension | |
|---|---|
| 2-(2,4-dichloro-5-ethoxyphenyl)-5,6,7,8-tetrahydro-1,2,4-triazolo-[4,3-A]-pyridin-3-(2H)-one | 50.0% |
| Polyacrylic acid thickener | 0.3% |
| Dodecylphenol polyethylene glycol ether | 0.5% |
| Disodium phosphate | 1.0% |
| Monosodium phosphate | 0.5% |
| Polyvinylalcohol | 1.0% |
| Pentachlorophenol | 0.4% |
| Water | 46.3% |

The ingredients are ground together in a sand mill to produce particles essentially all under 5 microns in size.

EXAMPLE 16

| Wettable Powder | |
|---|---|
| 2-(2,4-dichloro-5-methoxyphenyl)-5,6,7,8-tetrahydro-1,2,4-triazolo-[4,3-A]-pyridin-3-(2H)-one | 50% |
| Sodium alkylnaphthalenesulfonate | 2% |
| Sodium ligninsulfonate | 2% |
| Synthetic amorphous silica | 3% |
| Kaolinite | 43% |

The ingredients are thoroughly blended, passed through an air mill to produce an average particle size under 15 microns, reblended, and sifted through a U.S.S. No. 50 sieve (0.3 mm opening) before packaging.

EXAMPLE 17

| High-Strength Concentrate | |
|---|---|
| 2-(2 4-dichloro-5-methoxyphenyl)-5,6,7,8-tetrahydro-1,2,4-triazolo[4,3-A]pyridin-3(2H)-one | 99% |
| Trimethylnonyl polyethylene glycol ether | 1% |

The surfactant is sprayed on the active ingredient in a blender and the mixture sifted through a U.S.S. No. 40 sieve (0.42 mm openings) prior to packaging. The concentrate may be formulated further for field use.

EXAMPLE 18

| Low Strength Granule | |
|---|---|
| 2-[2,4-dichloro-5-(1-methoxyethoxy)-phenyl]2,5,6,7,8,9-hexahydro-3H-1,2,4-triazolo[4,3-A]-azepin-3-one | 0.5% |
| Attapulgite granules (low volatile matter; 0.59–0.25 mm., i.e. USS 30–60 mesh size) | 99.5% |

Forty grams of a solution containing 2.5% 2-[2,4-dichloro-5-(1-methylethoxy)phenyl]-2,5,6,7,8,9-hexahydro-3H-1,2,4-triazolo[4,3-A]-azepin-3-one dissolved in methyl alcohol are slowly atomized onto a fluidized bed of attapulgite granules (199 gm). Fluidization of the granules is continued after atomization is complete and until all the methyl alcohol is evaporated from the granules. The granules are packaged for use.

EXAMPLE 19

| Extruded Pellet | |
|---|---|
| 2-(2,4-dichloro-5-methoxyphenyl)-5,6,7,8-tetrahydro-1,2,4-triazolo-[4,3-A]-pyridin-3-(2H)-one | 25% |
| Anhydrous sodium sulfate | 10% |
| Crude Calcium ligninsulfonate | 5% |
| Sodium alkylnaphthalenesulfonate | 1% |
| Calcium/magnesium bentonite | 59% |

The ingredients are blended, hammer milled and moistened with about 10–12% water. The mixture is then extruded as cylinders about 3 mm in diameter which are cut to be about 3 mm long. These pellets may be used directly after drying or the dried pellets may be crushed to pass a U.S.S. No. 20 sieve (0.84 mm opening). The pellets retained on a U.S.S. No. sieve (0.42 mm openings) may be packaged for use and the fines recycled.

EXAMPLE 20

| Low Strength Granule | |
|---|---|
| 2-(2,4-dichloro-5-ethoxyphenyl)- 5,6,7,8-tetrahydro-1,2,4-triazolo- [4,3-A]pyridin-3(2H)-one | 0.2% |
| Anhydrous sodium sulfate | 10% |
| Crude Calcium ligninsulfonate | 5% |
| Sodium alkylnaphthalenesulfonate | 1% |
| Finely divided attapulgite clay | 83.8% |

The ingredients are blended, hammer milled and placed in a fluidized bed granulator. Water is aspirated into the fluidized bed of powder until small granules are formed. Water aspiration is then stopped but fluidization is continued to dry the formed granules. The granules are removed from the granulator and screened to pass a U.S.S. No. 20 sieve (0.84 mm opening). Granules retained on a U.S.S. N. 40 sieve (0.42 mm opening) are packaged for use. Granules larger than 0.84 mm are ground and recycled. Fines smaller than 0.42 mm are also recycled.

EXAMPLE 21

| Extruded Pellet | |
|---|---|
| 2-(2,4-dichloro-5-methoxyphenyl)- 5,6,7,8-tetrahydro-1,2,4-triazolo- [4,3-A]-pyridin-3-(2H)-one | 0.1% |
| Anhydrous sodium sulfate | 10% |
| Crude Calcium ligninsulfonate | 5% |
| Sodium alkylnaphthalenesulfonate | 1% |
| Polyoxyethylene (4 × 10$^6$ average molecular weight) | 1% |
| Calcium/magnesium bentonite | 82.9% |

The ingredients are blended, hammer milled and then moistened with about 12% water. The moist mixture is extruded as cylinders about 1 mm in diameter and about 2 mm long. These small pellets are dried and packaged. They are applied directly.

EXAMPLE 22

| Low Strength Granule | |
|---|---|
| 2-[2,4-dichloro-5-(1-methylethoxy)- phenyl]-5,6,7,8-tetrahydro-1,2,4- triazolo[4,3-A]-pyridin-3(2H)-one | 0.05% |
| Dimethylformamide | 5% |
| Attapulgite granules (low volatile matter; 0.59-0.25 mm i.e. U.S.S. No. 30-60 mesh size) | 94.95 |

One-tenth of a gram of 2-[2,4-dichloro-5-(1-methylethoxy)phenyl]-5,6,7,8-tetrahydro-1,2,4-triazolo[4,3-A]-pyridin-3(2H)-one is dissolved in 9.9 grams of dimethylformamide. This solution is very slowly atomized onto 190.1 grams of a rapidly tumbling bed of the attapulgite granules. After application of the active is complete, the formulation is blended for a few additional minutes. The dimethylformamide is not removed from the formulation. The granules are packaged for use.

EXAMPLE 23

| Emulsifiable Concentrate | |
|---|---|
| 2-[2,4-dichloro-5-(1-methylethoxy)- phenyl]-5,6,7,8-tetrahydro-1,2,4- triazolo[4,3-A]-pyridin-3(2H)-one | 10% |
| Blend of oil-soluble sulfonate with polyoxyethylene ethers | 6% |
| Aromatic hydrocarbon solvent with a Tag closed cup flash point between 100 and 115° F. | 84% |

The ingredients are combined and stirred until solution is complete. The solution is filtered through a fine screen filter prior to packaging to remove any extraneous undissolved material.

EXAMPLE 24

| Low Strength Granules | |
|---|---|
| 2-[2,4-dichloro-5-(1-methylethoxy)- phenyl]-2,5,6,7,8,9-hexahydro-3H- 1,2,4-triazolo[4,3-A]-azepin-3-one | 0.1% |
| Sodium ligninsulfonate | 5% |
| Preformed sand granules having a particle size distribution from U.S.S. sieve No. 140 (150 microns) to U.S.S. sieve No. 50 (297 microns) | 94.9% |

0.5 Gram 2-[2,4-dichloro-5-(1-methylethoxy)phenyl]-2,5,6,7,8,9-hexahydro-3H-1,2,4-triazolo[4,3-A]-azepin-3-one and 25 gm sodium ligninsulfonate are dissolved in 50 gm water. This solution is slowly sprayed onto a tumbling bed of the sand granules (474.5 g). After spraying is complete, the tumbling granules are warmed to remove the water. The resulting granules are packaged for use.

The compounds of Formula I can also be combined with other herbicides and are particularly useful in combination with s-triazines such as atrazine [2-chloro-4-(ethylamino)-6-(isopropylamino)-s-triazine], linuron [3-(3,4-dichlorophenyl)-1-methoxy-1-methylurea], alachlor [2-chloro-2',6'-diethyl-N-(methoxymethyl)-acetanilide, bromacil [3-(sec-butyl)-5-bromo-6-methyluracil], diuron [3-(sec-butyl)-5-bromo-6-methyluracil], 3-cyclohexyl-1-methyl-6-dimethylamino-s-triazine-2,4(1H,3H)-dione, paraquat [1,1'-dimethyl-4,4'-bipyridinum ion], m-(3,3-dimethylureido)-phenyl-tert-butylcarbamate, 2-methyl-4-chlorophenoxyacetic acid, its salts or esters, 4-amino-6-tert-butyl-3-methylthio-as-triazin-5(4H)-one, aryl 4-nitrophenyl ethers such as 2,4,6-trichlorophenyl 4-nitrophenyl ether and 2,4-dichlorophenyl 4-nitrophenyl ether, methyl-m-hydroxy carbanilate-m-methylcarbanilate, S-(2,3,3-trichloroallyl)-diisopropylthiocarbamate, S-(2,3-dichloroallyl)diisopropylthiocarbamate, 3-cyclohexyl-5,6-trimethyleneuracil, S-ethyl-N-ethylthiocyclohexanecarbamate, 5-amino-4-chloro-2-phenyl-3(2H)-pyridazinone, 4-amino-3-methyl-6-phenyl-1,2,4-triazin-5(4H)-one for controlling a broad spectrum of weeds.

UTILITY

The compounds of Formula I are useful for the selective preemergence control of undesired vegetation, in crops such as corn, sugar beets and wheat. Compounds of this invention may be used as directed treatments for the pre- or postemergence control of weeds in various crops including corn and cotton.

The precise amount of the compounds of Formula I to be used in any given situation will vary according to the particular end result desired, the use involved, the crop and weed species, and soil involved, the formulation used, the mode of application, prevailing weather conditions, foliage density and like factors. Since so many variables play a role, it is not possible to state a rate of application suitable for all situations. Broadly speaking, the compounds of the invention are used at levels of about 0.015 to about 15 kilograms per hectare, preferably about 0.03 to about 10 kilograms per hectare. The lower rates in this range will generally be selected on lighter soils, soils low in organic matter content, for selective weed control in crops, or in situations where maximum persistence is not necessary.

Herbicidal activity of the subject compounds was discovered in a number of greenhouse tests. The test procedure was as follows:

EXAMPLE 25

Seeds of crabgrass (Digitaria spp.), barnyardgrass (*Echinochloa crusgalli*), wild oats (*Avena fatua*), *Cassia tora*, morningglory (Iopmoea spp.), cocklebur (Xanthium spp.), sorghum, corn, soybean, rice, wheat and nutsedge tubers were planted in a growth medium and treated preemergence with the chemicals dissolved in a non-phytotoxic solvent. At the same time, cotton having five leaves (including cotyledonary ones), bush beans with the third trifoliate leaf expanding, crabgrass with two leaves, barnyardgrass with two leaves, wild oats with one leaf, Cassia with three leaves (cotyledonary ones), morningglory with four leaves (including the cotyledonary ones), cockelbur with four leaves (including the cotyledonary ones), sorghum with three leaves, corn with three leaves, soybean with two cotyledonary leaves, rice with two leaves, wheat with one leaf, and nutsedge with three-five leaves were sprayed. Treated plants and controls were maintained in a greenhouse for sixteen days, whereupon all species were compared to controls and visually rated for response to treatment. The ratings are based on a numerical scale extending from 0=no injury, to 10=complete kill. In the tables of tabulated data the ampersands represent the value 10. The accompanying descriptive symbols have the following meanings: B=burn; G=growth retardation; C=chlorosis/necrosis; D=defoliation; E=emergence inhibition; and H=formative effects. The pre- and post-emergence ratings for the compounds tested by this procedure are shown in Table I.

The data illustrate the herbicidal potency of the claimed compounds.

TABLE I

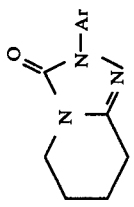

| Cpd. No. | Ar = | Mode of Appln. | Rate Kg/Ha | Bush Bean | Cotton | Morning-glory | Cocklebur | Cassia | Nutsedge | Crabgrass | Barnyard-grass | Wild Oats | Wheat | Corn | Soybean | Rice | Sorghum |
|---|---|---|---|---|---|---|---|---|---|---|---|---|---|---|---|---|---|
| 1 | 4-CH₃, 3-Cl phenyl | Post<br>Pre | 2.0<br>2.0 | 9B | 9B | &B<br>&C | 7B<br>&C | 6B<br>&C | 6B<br>&C | &B<br>&C | &B<br>&C | 6B<br>&C | 6B<br>&C | 8B<br>&C | 9B<br>9C | 7B<br>&C | 9B<br>&C |
| 2 | 4-Cl, 2-Br, (methyl) phenyl | Post<br>Post<br>Pre | 2.0<br>2.0<br>2.0 | 9B | 8B | 9B<br>&C | 7B<br>&C | 7B<br>&C | 2B<br>7C<br>9C | &C<br>&C | &C<br>&C | 6B<br>&C | 8B<br>&C | 7B<br>&C | 9B<br>&C | 8B<br>&C | 9B<br>&C |
| 3 | 3,5-diCl, 2-methyl phenyl | Post<br>Post<br>Pre | 0.4<br>0.4<br>0.4 | 9B | 9B | &B<br>&C | 7B<br>&C | 6B<br>&C | 2B<br>7C<br>&E | &B<br>&C | &B<br>&E | 8B<br>&C | 9B<br>&C | 6B<br>&C | 8B<br>&C | 6B<br>&C | 9B<br>&C |
| 4 | cyclopentyloxy-2,4-diCl phenyl | Post<br>Pre | 0.4<br>0.4 | &B | &B | &B<br>&C | 9B<br>9C | 7B<br>9C | 6B<br>&C | 7B<br>&E | &B<br>&C | 6B<br>9C | 5B<br>9C | 6B<br>9H | 9B<br>9H | 7B<br>9C | 7B<br>&C |
| 5 | tetrahydrothiopyranyloxy-2,4-diCl phenyl | Post<br>Pre<br>Pre | 0.4<br>0.4<br>0.4 | &B | &B | 9B<br>9C | 8B<br>2C | 7B<br>9C | 5B<br>8C | 9B<br>&C | 9B<br>&C | 4B<br>9C | 6B<br>1C<br>3H | 8B<br>9H | 9B<br>8H | 7B<br>&C | 6B<br>9C |

TABLE I-continued

| | | | | | | | | | | | | | | | | | | |
|---|---|---|---|---|---|---|---|---|---|---|---|---|---|---|---|---|---|---|
| 6 | O(CH$_2$)$_2$OCH$_2$CH$_3$  | Post Post Pre | 0.4 0.4 0.4 | &B | 9B | &B &C | 8B &C | 4B 9C | 8B 9C | 4B 8H &E | 9B &E | 7B 9C | 8B 9C | 4B 9H | 9B &H | 8B &C | 9B &E |
| 7 | OCH$_2$CH(CH$_3$)$_2$  | Post Post Pre Pre | 0.4 0.4 0.4 0.4 | 9B | 9B | &B &C | 9B 1C 8H | 7B 0 | 4B 9C | &B &E | &B &E | &B 9C | 9B 9C | 3B 7H 3C 9H | 9B &H | 6B &C | 9B &C |
| 8 | OCH$_2$CH=CH$_2$  | Post Pre | 0.4 0.4 | &B | &B | &B &C | &B &C | 9B &C | 9B &C | &B &C | &B &C | &B &C | 9B &C | 8B 9H | &B &H | &B &C | &B &C |
| 9 | CH$_3$ O—CHCH$_2$CH$_3$  | | | | | &B &C | 9B 9H | &B &C | 8B &C | &B &C | &B &C | &B &C | 8B &C | 7B 9H | 9B &C | 9B &C | &B &C |
| 10 | OCH(CH$_3$)$_2$  | Post Pre | 0.4 0.4 | 9B | 9B | &B &C | 9B &C | &B &C | 9B &C | &B &C | &B &C | &B &C | 6B 9C | 6B 5H &C | 9B &C | &B &C | &B &C |
| 11 | OH  | Post Post Pre Pre | 2.0 2.0 2.0 2.0 | 9B | 9B | &B 2C 8G | 6B 8G | 5B 2C 8G | 4B 8C | &B &C | &B &C | &B &C | 7B 9H &C | 6B 5H &C | 9B 3C 9H | &B &C | &B &C |

TABLE I-continued

| # | Structure | | | | | | | | | | | | | | | | | |
|---|---|---|---|---|---|---|---|---|---|---|---|---|---|---|---|---|---|---|
| 12 | CH₃—$\bigcirc$—OCHCH₂CH₃ (2,4-diCl, methyl) | Post Pre Pre | 0.4 0.4 0.4 | &B | 9B | &B 1C 8G | 9B 0 | 6B 0 | 3B 9C | 7B 9H | &B &C | 4B &C | 5B 9C | 5B 3C 8H | 9B 6H | 6B &C | 9B &C |
| 13 | OCH₂CH₂CH₃—$\bigcirc$ (2,4-diCl, methyl) | Post Pre | 0.4 0.4 | &B | 9B | &B &C | 8B 4H | 9B &E | 8B 9C | &B &C | &B &C | 9B &C | 5B &C | 8B 2C 8H | 9B 1C 9H | 7B 9C | 9B &C |
| 14 | OCH₂CH₂CH₃—$\bigcirc$ (2,4-diCl, methyl) | Post Pre Pre | 0.4 0.4 0.4 | &B | &B | &B &C | &B 1C 7H | &B &C | &B 9C | &B &C | &B &C | 9B &C | 8B &C | 8B 9H | &B &H | 9B &C | 9B &C |
| 15 | OCH₂CH₃—$\bigcirc$ (2,4-diCl, methyl) | Post Pre | 0.4 0.4 | &B | &B | &B &C | 9B 9C | &B &C | 9B &C | &B &C | &B &C | 9B &C | 9B &C | 9B 9H | 9B &H | &B &C | &B &C |
| 16 | CH₃—$\bigcirc$—CH₃ (diCl, CH₃) | Post Pre | 0.4 0.4 | 6B | 7B 6D | 9B 2C | 5B 2C | 1B 2C | 1B 0 | 1B 4H 1C 9H | 2B 9C | 2B 9C | 2B 9H | 6B 9H | 3B 8C | 3B &H |
| 17 | OCH₃—$\bigcirc$ (methyl) | Post Pre | 2.0 2.0 | 9B | 8B 8D | 9B 1C 3H | 1B 1C 4G | 2B 5C | 1B 5C | 7B | 2B 9C | 2B 9C | 3B 2C 9H | 5B 3C | 3B 3C | 6B &C |
| 18 | Br—$\bigcirc$—Cl | Post Pre | 2.0 2.0 | &B | 9B | 9B &C | 7B &C | 8B &C | 8B &C | &B &C | &B &C | 9B &C | 9B &C | 9B &C | 9B &C | 9B &C | 9B &C |

TABLE I-continued

| # | Structure | Timing | Rate | | | | | | | | | | | | | | | | |
|---|---|---|---|---|---|---|---|---|---|---|---|---|---|---|---|---|---|---|---|
| 19 | 2,6-difluoro-4-methylphenyl (F, F, CH₃) | Post<br>Pre<br>Pre | 2.0<br>2.0<br>2.0 | 8B | 8B | 7B<br>1C<br>6H | 5B<br>1C<br>7G | 3B<br>9C | 2B<br>&C | 9B<br>9C | 3B<br>&C | 4B<br>9C | 3B<br>9C | 3B<br>8C | 5B<br>9H | 3B<br>9C | 3B<br>9C |
| 20 | 3-chloro-4-fluoro-methylphenyl | Post<br>Post<br>Pre<br>Pre | 0.4<br>0.4<br>0.4<br>0.4 | 9B | 9B | 9B | 7B<br>9C | 6B<br>&C | 5B<br>&C | &B<br>&C | &B<br>&C | 9B | 5B<br>6H<br>&C | 7B<br>9C | 7B<br>&C | 7B<br>&C |
| 21 | 4-chloro-methylphenyl | Post<br>Pre<br>Pre | 0.4<br>0.4<br>0.4 | 8B | 8B | 6B<br>0 | 3B<br>0 | 3B<br>0 | &C | 9B<br>&C | &C | 2B<br>&C | 1C<br>9H<br>9C | 2C<br>6G | &C | 7B<br>&C |
| 22 | 3-chloro-4-nitrophenyl | Post<br>Pre<br>Pre | 0.4<br>0.4<br>0.4 | 7B | 7B | 8B<br>&C | 5B | 2B<br>2H | 3B<br>0 | 5B<br>9H<br>1C<br>9H | 9B<br>&C | 2B<br>9C | 1B<br>9C<br>9H | 2C<br>6G | 1B<br>8C | 7B<br>2C<br>7G |
| 23 | 4-cyanophenyl | Post<br>Post<br>Pre<br>Pre | 2.0<br>2.0<br>2.0<br>2.0 | 5B | 5B | 7B<br>1C<br>9H | 2B<br>1C | 2B<br>4H | 6B<br>3C | 3B<br>&C | 9B<br>&C | 3B | 3B<br>9C | 2B | 5B | 3B |
| 24 | 4-methylphenyl | Post<br>Post<br>Pre<br>Pre<br>Pre | 2.0<br>2.0<br>0.4<br>0.4<br>0.4 | 8B | 8B | 8B<br>2C | 4B<br>0 | 3B<br>— | 1B<br>5C | 9B<br>&C | 6B<br>&C | 2B<br>8C | 1B<br>9C | 5B<br>5C<br>9H<br>3B<br>2C | 5B<br>1C<br>9H<br>3B<br>2C | 4B<br>— |
| 25 | 2,5-dichloro-4-methylphenyl | Post<br>Pre<br>Pre | 0.4<br>0.4<br>0.4 | 6B | 6B | 4B<br>1H | 2B<br>0 | 1B<br>— | 1B<br>0 | 5B<br>9C | 5B<br>9C | 1B<br>7C | 2C<br>6G<br>4H | 8C | 1C<br>5G | 3B<br>9H |
| 26 | 2-chloro-5-methylphenyl | Post<br>Pre<br>Pre | 2.0<br>2.0<br>2.0 | 9B | 9B | 9B<br>9H | 7B<br>1C<br>3H | 4B<br>— | 5B<br>7C | &B<br>&C | 5B<br>9C | 7B<br>&C | 1B<br>7C | 6B<br>9C | 8B<br>8H | 2B<br>9C | 3B<br>9H |
| | 3-chloro-4-methylphenyl | Post<br>Pre | 0.4<br>0.4 | 9B | 9B | 9B<br>&C | 4B<br>&C | 4B<br>— | 6B<br>9C | &B<br>&C | 8B<br>&C | 5B<br>&C | 5B<br>&C | 6B<br>9C | 8B<br>9H | 8B<br>9C | 8B<br>&C |
| | 3,5-dichlorophenyl | | | | | | | | | | | | | | | 5B<br>9C | 7B<br>&C |

TABLE I-continued

| Cpd. No. | Ar = | Mode of Appln. | Rate Kg/Ha | Bush Bean | Cotton | Morning-glory | Cocklebur | Cassia | Nutsedge | Crabgrass | Barnyard-grass | Wild Oats | Wheat | Corn | Soybean | Rice | Sorghum |
|---|---|---|---|---|---|---|---|---|---|---|---|---|---|---|---|---|---|
| 27 | 2,4-Cl, 5-OCH(CH₃)₂, methyl-phenyl | Post | 0.4 | &B | &B | &B &C | 9B &C | &B &C | 9B &C | &B &C | &B &C | &B &C | 9B &C | 8B &C | 9B &C | &B &C | &B &C |
|  |  | Pre | 0.4 |  |  |  | &C |  | &C | &C | &C | &C | &C | &C | &C |  |  |
| 28 | 2,4-Cl, methyl-phenyl | Post | 2.0 | &B | &B | &B | 8B &C | &B &C | 9B &C | &B &C | &B &C | &B &C | 9B &C | 9B &C | 9B &C | 9B &C | 9B &C |
|  |  | Pre | 2.0 |  |  | 9C | &C | &C | &C | &C | &C | &C | &C | &C | 9C | 7B 9B | &C |
|  |  | Post | 0.4 | 9B | 9B | 8B | 7B | 5B | 4B | 8B | 9B | 9B | 8B | 8B | 8B | 9B |  |
|  |  | Pre | 0.4 |  |  | 9H | &E | &C | &C | &C | &C | &C | &C | &C | 9H | &C |  |
| 29 | 2-Cl, 4-OCH₃, methyl-phenyl | Post | 0.4 | 9B | 9B | &B | 7B | 8B | 9B | &B | &B | 8B | 9B | 9B | 9B | 9B | 9B |
|  |  | Pre | 0.4 |  |  | &C | &C | &C | &C | &C | &C | &C | &C | &C | &C | &C | &C |

| Cpd. No. | Ar = | Mode of Appln. | Rate Kg/Ha | Bush Bean | Cotton | Morning-glory | Cocklebur | Cassia | Nutsedge | Crabgrass | Barnyard-grass | Wild Oats | Wheat | Corn | Soybean | Rice | Sorghum |
|---|---|---|---|---|---|---|---|---|---|---|---|---|---|---|---|---|---|
| 30 | 2,4-Cl-phenyl | Post | 2.0 |  |  |  | 9B &C | 9B &C | 8B 9C | &B &C | &B &C | &B &C | 9B &C | 9B &C | 9B &C | 8B 9C | &B &C |
|  |  | Pre | 2.0 |  |  |  |  |  |  |  |  |  |  |  |  |  |  |
| 31 | 2-Cl, 4-OCH₃, methyl-phenyl | Post | 2.0 |  |  |  | 9B &C | 7B &C | 8B 9C | &B &C | &B &C | &B &C | &B &C | 9B &C | 9B &C | 9B &C | &B &C |
|  |  | Pre | 2.0 |  |  |  |  |  |  |  |  |  |  |  |  |  |  |

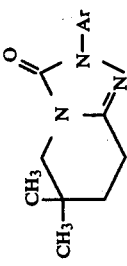

TABLE I-continued

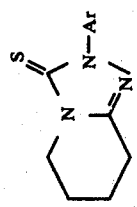

| Cpd. No. | Ar = | Mode of Appln. | Rate Kg/Ha | Bush Bean | Cotton | Morning-glory | Cocklebur | Cassia | Nutsedge | Crabgrass | Barnyard-grass | Wild Oats | Wheat | Corn | Soybean | Rice | Sorghum |
|---|---|---|---|---|---|---|---|---|---|---|---|---|---|---|---|---|---|
| 32 | OCH₃, Cl, Cl | Post Post Pre Pre | 0.4 0.4 0.4 0.4 | 9B | 9B | &B &C | 8B 3C 6H | 5B 9C | 5B 7C 9C | 9B &C | 9B &C | 5B 5H &C | 5B 6H &C | 8C 9C | 9B 9C | 7B 9C | 9B &C |
| 33 | Br, F | Post Pre Pre | 0.4 0.4 0.4 | 9B | 9B | &B 9C | 9B &E | 9B &E | 5B 5C | 7B &C | 7B &C | 3B 9C | 5B 9C | 7B 4C 8H | 9B &C | 6B 9C | 9B 9H |
| 34 | OCH₃, Cl, Cl | Post Pre Pre | 0.4 0.4 0.4 | &B | &B | &B &C | 8B &C | 8B &C | 5B 8C | 9B &C | 8B &C | 6B &C | 6B &C | 5B 9C | 9B 2C 9H | 8B &C | 9B &C |
| 35 | Cl, Cl | Post Pre Pre | 0.4 0.4 0.4 | 9B | 9B | &B 2C 8H | 8B 1C 8G | 9B &C | &B 8C | 9B &C | 8B &C | 7B &C | 5B &C | 5B 2C 8H | 8B 2C 9H | 6B 9C | 7B 9C |
| 36 | OCH(CH₃)₂, Cl, Cl | Post Pre Pre | 0.4 0.4 0.4 | 8B | &B | &B &C | &B &E | 7B &C | 8B 9C | &B &C | &B &C | 7B &C | 6B 9C | 7B 3C 7H | 9B 9H | 9B &C | 9B &C |

TABLE I-continued

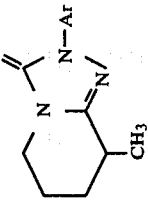

| Cpd. No. | Ar = | Mode of Appln. | Rate Kg/Ha | Bush Bean | Cotton | Morning-glory | Cocklebur | Cassia | Nutsedge | Crabgrass | Barnyard-grass | Wild Oats | Wheat | Corn | Soybean | Rice | Sorghum |
|---|---|---|---|---|---|---|---|---|---|---|---|---|---|---|---|---|---|
| 37 | 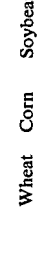 | Post<br>Pre | 0.4<br>0.4 | &B<br> | 8B<br> | &B<br>9H | 5B<br>&C | &B<br>&C | 5B<br>9C | &B<br>&C | 7B<br>&C | 6B<br>&C | 5B<br>&C | 5B<br>9H | 9B<br>9H | 9B<br>9C | 8B<br>9C |
| 38 | 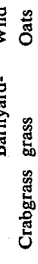 | Post<br>Post<br>Pre<br>Pre | 0.4<br>0.4<br>0.4<br>0.4 | 8B<br><br><br> | 8B<br>6D<br><br> | &B<br>3C<br><br> | 5B<br>1C<br>9H<br> | 1B<br>&C<br><br> | 1B<br>8C<br><br> | 6B<br>&C<br><br> | 9B<br>&C<br><br> | 4B<br>&C<br><br> | 3B<br>9C<br><br> | 7B<br>9H<br><br> | 6B<br>9H<br><br> | 5B<br>9C<br><br> | 6B<br>9C<br><br> |
| 39 |  | Post<br>Post<br>Pre | 0.4<br>0.4<br>0.4 | 8B<br><br> | 9B<br>5D<br> | &B<br>&C<br> | 6B<br>9C<br> | 5B<br>&C<br> | 7B<br>&C<br> | 9B<br>&C<br> | 9B<br>&C<br> | 6B<br>8H<br>&C | 6B<br>&C<br> | 5B<br>9H<br>&C | 9B<br>9H<br> | 7B<br>&C<br> | 9B<br>&C<br> |
| 40 | 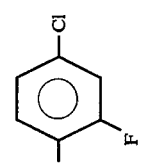 | Post<br>Post<br>Pre | 0.4<br>0.4<br>0.4 | 9B<br><br> | 9B<br><br> | &B<br>9H<br> | 8B<br>&E<br> | 9B<br>&C<br> | &B<br>&C<br> | 5B<br>9H<br>&C | &B<br>&C<br> | 6B<br>8H<br>&C | 6B<br>3H<br>9C | 3B<br>7H<br>9H | 6B<br>9H<br> | 8B<br>9C<br> | 6B<br>9H<br>&C |

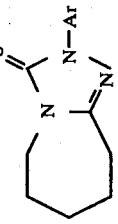

| Cpd. No. | Ar = | Mode of Appln. | Rate Kg/Ha | Bush Bean | Cotton | Morning-glory | Cocklebur | Cassia | Nutsedge | Crabgrass | Barnyard-grass | Wild Oats | Wheat | Corn | Soybean | Rice | Sorghum |
|---|---|---|---|---|---|---|---|---|---|---|---|---|---|---|---|---|---|

TABLE I-continued

| Cpd. No. | Ar = | Mode of Appln. | Rate Kg/Ha | Bush Bean | Cotton | Morning-glory | Cocklebur | Cassia | Nutsedge | Crabgrass | Barnyard-grass | Wild Oats | Wheat | Corn | Soybean | Rice | Sorghum |
|---|---|---|---|---|---|---|---|---|---|---|---|---|---|---|---|---|---|
| 41 | 4-NO2, 2-CH3 phenyl | Post | 2.0 | 5B 6Y | 9B | 5B | 5B | 2B | 1B | 5B | 5B | 1B | 1B | 2B | 3B | 2B | 3B |
|  |  | Post | 2.0 |  |  | 2G | 0 | 0 | 0 | 5G | 9C | 8C | 7C | 6C | 1H | 9C | 1C |
|  |  | Pre | 2.0 |  |  |  |  |  |  |  |  |  |  |  |  |  | 6G |
|  |  | Pre | 2.0 |  |  |  |  |  |  |  |  |  |  |  |  |  |  |
| 42 | 4-Cl, 2-CH3 phenyl | Post | 2.0 | &B | &B | 9B | 9B | 3B | 3B | 6B | 9B | 3B | 2B | 3B | 6B | 6B | 5B |
|  |  | Post | 2.0 |  |  | 5G | 3G | 2H | 1C | 9H | &C | 9C | 9C | 5C | 7G | 5C | 3C |
|  |  | Pre | 2.0 |  |  |  |  |  | 6G |  |  |  | 9H |  |  | 9H | 7H |
| 43 | 2-Cl, 4-OCH(CH3)2, 5-CH3 phenyl | Post | 0.4 | 9B | 9B | &B | 2B | 9B | 4B | 9B | 9B | 7B | 7B | 6B | 9B | 9B | 8B |
|  |  | Post | 0.4 |  |  | 5H | 9H |  | 9C |  | &C | 9C | 9C | &H | 9H | &C |  |
|  |  | Pre | 0.4 |  |  |  | 0 |  |  |  |  |  |  |  |  |  |  |
| 44 | 2-Cl, 4-OCH3, 5-CH3 phenyl | Post | 0.4 | 9B | 8B 8D | &B | 9B | 9B | 5B | 9B | 9B | 5B | 5B | 4B | 8B | 5B | 4B |
|  |  | Post | 0.4 |  |  | 3G | 1C | 0 | 7C | 9C | &C | 9C | 9C | &H | 1C | 9C | &C |
|  |  | Pre | 0.4 |  |  |  |  |  |  |  |  |  |  |  | 7G |  |  |

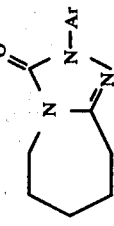

| Cpd. No. | Ar = | Mode of Appln. | Rate Kg/Ha | Bush Bean | Cotton | Morning-glory | Cocklebur | Cassia | Nutsedge | Crabgrass | Barnyard-grass | Wild Oats | Wheat | Corn | Soybean | Rice | Sorghum |
|---|---|---|---|---|---|---|---|---|---|---|---|---|---|---|---|---|---|
| 45 | 4-Cl, 3-F, 2-CH3 phenyl | Post | 2.0 | 9B | 9B | 9B | 7B | 5B | 7B | &B | &B | 9B | 8B | 7B | 9B | 9B | 7B |
|  |  | Post | 2.0 |  |  | 9C | &C | &C | 9C | &C | &C | &C | &C | &H | 9H | 9C | 9H |
|  |  | Pre | 2.0 |  |  |  |  |  |  |  |  |  |  |  |  |  | &C |
| 46 | 2-Cl, 4-OCH3, 5-CH3 phenyl | Post | 0.4 | &B | 9B | &B | 6B | 5B | 7B | 4B | 9B | 9B | 7B | 6B | 8B | 9B | 9B |
|  |  | Post | 0.4 |  |  | 9G | 6G | 6C | 9C | 9H | &C | &C | &C | &C | 1C | 9C | &C |
|  |  | Pre | 0.4 |  |  |  |  |  |  | &C |  |  |  |  | 9H |  |  |
|  |  | Pre | 0.4 |  |  |  |  |  |  |  |  |  |  |  |  |  |  |

TABLE I-continued

| Cpd. No. | Ar | Mode of Appln. | Rate Kg/Ha | Bush Bean | Cotton | Morning-glory | Cocklebur | Cassia | Nutsedge | Crabgrass | Barnyard-grass | Wild Oats | Wheat | Corn | Soybean | Rice | Sorghum |
|---|---|---|---|---|---|---|---|---|---|---|---|---|---|---|---|---|---|
| 47 | 2,4-Cl2-OCH(CH3)2-phenyl | Post | 0.4 | 9B | 9B | &B 1C 8G | 5B &G | 9B 9C | 8B 9C | 9B &C | 9B &C | 8B &C | 7C 9C | 6B &C | 9B 9H | &B 9C | 8B &C |
|  |  | Pre | 0.4 |  |  |  |  |  |  |  |  |  |  |  |  |  |  |
|  |  | Pre | 0.4 |  |  |  |  |  |  |  |  |  |  |  |  |  |  |
| 48 | 2,5-Cl2-phenyl | Post | 2.0 | 9B | 9B | &B 9H | 5B 8H | 3B &C | 9B 9C | 9B &C | &B &C | &B &C | 3B 9C | 9B &C | 8B 9H | 9B 1C 8H | 9B 9C | 9B &C |
|  |  | Pre | 2.0 |  |  |  |  |  |  |  |  |  |  |  |  |  |  |
| 49 | 4-F-phenyl | Post | 2.0 | 3B | 5B 9D | 1B | 1B | 1B | 0 | 1B | 2B | 4B | 3B | 2C | 1B | 4B | 1B | 4B |
|  |  | Post | 2.0 |  |  |  |  |  |  |  |  |  |  |  |  |  |  |
|  |  | Pre | 2.0 |  |  | 1C | 0 | 0 | 0 | 5G | 9C | 8C | 8C | 5C | 1C 5G | 2C | 2C |
|  |  | Pre | 2.0 |  |  |  |  |  |  |  |  |  |  |  |  |  |  |

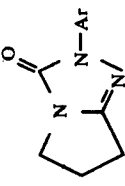

| Cpd. No. | Ar | Mode of Appln. | Rate Kg/Ha | Bush Bean | Cotton | Morning-glory | Cocklebur | Cassia | Nutsedge | Crabgrass | Barnyard-grass | Wild Oats | Wheat | Corn | Soybean | Rice | Sorghum |
|---|---|---|---|---|---|---|---|---|---|---|---|---|---|---|---|---|---|
| 50 | 2,4-Cl2-phenyl | Post | 2.0 | 9B | 9B | &B 9C 9H | 7B 1C 2H | 2B 1C 5G | 2B 7H | 9B &C | 6B &C | 3B 9C | 3B &C | 3B 5C 9H | 8B 1C 9H | 6B 9C | 8B &C |
|  |  | Pre | 0.4 |  |  |  |  |  |  |  |  |  |  |  |  |  |  |
|  |  | Pre | 0.4 |  |  |  |  |  |  |  |  |  |  |  |  |  |  |
| 51 | 2,4-Cl2-OCH3-phenyl | Post | 0.4 | 8B | 9B | 5B 2H | 2B 1H | 2B 5C | 2B 0 | 7B &C | 6B &C | 3B 9C | 3B 9C | 3B 5C 9H | 6B 1C 5H | 4B 5C | 6B 8C |
|  |  | Pre | 0.4 |  |  |  |  |  |  |  |  |  |  |  |  |  |  |
|  |  | Pre | 0.4 |  |  |  |  |  |  |  |  |  |  |  |  |  |  |
| 52 | 2,4-Cl2-OCH(CH3)2-phenyl | Post | 0.4 | 9B | 9B | &B &C | 3B 1C 5G | 2B 1C 5G | 2B 9C | 9B &C | 4B &C | 3B &C | 3B &C | 5B &C | 8B 9H | 3B &C | 5B &C |
|  |  | Pre | 0.4 |  |  |  |  |  |  |  |  |  |  |  |  |  |  |
|  |  | Pre | 0.4 |  |  |  |  |  |  |  |  |  |  |  |  |  |  |
| | 2,4-Cl2-OCH(CH3)2-phenyl | Post | 0.4 | | | &B 9C | 7B 1C 2H | 5B 1C 5G | 8B &C | 9B &C | &B &C | 6B &C | 5B &C | 4B 2C 9H | 7B &E | 7B &C | 9B &C |
|  |  | Pre | 0.4 |  |  |  |  |  |  |  |  |  |  |  |  |  |  |
|  |  | Pre | 0.4 |  |  |  |  |  |  |  |  |  |  |  |  |  |  |

EXAMPLE 26

Two plastic bulb pans were filled with fertilized and limed Fallsington silt loam. One pan was planted with corn, sorghum and several grassy weeds. The other pan was planted with soybeans, purple nutsedge (*Cyperus rotundus*), and several broadleaf weeds. The following grassy and broadleaf weeds were planted: crabgrass (*Digitaria sanguinalis*), barnyardgrass (*Echinochloa crusgalli*), wild oats (*Avena fatua*), johnsongrass (*Sorghum halepense*), giant foxtail (*Setaria faberii*), Kentucky bluegrass (*Poa pratensis*), cheatgrass (*Bromus secalinus*), mustard (*Brassica arvensis*), cocklebur (*Xanthium pennsylvanicum*), pigweed (*Amaranthus retroflexus*), morningglory (*Ipomoea hederacea*), cassia (*Cassia tora*), teaweed (*Sida spinosa*), velvetleaf (*Abutilon theophrasti*), and jimsonweed (*Datura stramonium*). A 5-inch diameter paper cup was also filled with prepared soil and planted with rice and wheat. Another 5-inch cup was planted with sugarbeets. The above four containers were treated preemergence (compound sprayed on soil surface before seed germination) with the test compounds. Twenty-eight days after treatment, the plants were evaluated and the data recorded as set forth in Table II: zero=no response; 10=maximum response.

Good control of a wide spectrum of weeds at low rates and selectivity on such crops as corn, sugar beets and wheat are shown in these data.

TABLE II

PRE-EMERGENCE ON FALLSINGTON SILT LOAM

| COMPOUND | Rate, kg/ha | Crab-grass | Barn-yard-grass | Sor-ghum | Wild Oats | John-son-grass | Dal-lis-grass | Giant Foxtail | Ky. blue-grass | Cheat-grass | Sugar-beets | Corn | Mus-tard |
|---|---|---|---|---|---|---|---|---|---|---|---|---|---|
|  | 0.03 | 7H | 6H | 3H | 2H | 8H | 8H | 4H | 6H | 2H | 5H | 0 | 9H |
| | 0.06 | 10H | 10H | 4H | 6H | 10H | 9H | 8H | 8H | 5H | 6H | 2C | 10H |
| | 0.12 | 10H | 10H | 6H | 9H | 10H | 10H | 9H | 10H | 6H | 10H | 2C | 10H |
|  | 0.12 | 8H | 6H | 6H | 4H | 9H | 7H | 8H | 7H | 4H | 3H | 0 | 4G |
| | 0.50 | 10H | 10H | 10H | 8H | 10H | 9H | 10H | 10H | 7H | 6H | 4H | 10H |
|  | 0.06 | 10E | 10H | 9H | 8C | 10H | 10H | 10H | 10H | 8H | 10C | 0 | 10E |
| | 0.12 | 10E | 10H | 10H | 9C | 10H | 10H | 10E | 10E | 9H | 10C | 0 | 10E |
| | 0.50 | 10E | 10E | 10H | 10C | 10H | 10H | 10E | 10E | 10H | 10C | 5H | 10E |
| 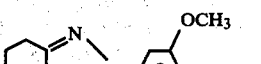 | 0.06 | 10H | 7H | 6H | 6H | 7H | — | 10H | 9H | 2H | 9H | 0 | 10C |
| | 0.25 | 10H | 10H | 10H | 10H | 10H | — | 10H | 10H | 9H | 10H | 4H | 10C |

| COMPOUND | Rate kg/ha | Cock-lebur | Pig-weed | Nut-sedge | H. Indigo | Morn-ing-glory | Cas-sia | Tea-weed | Vel-vet-leaf | Jim-son-weed | Soy-bean | Rice | Wheat |
|---|---|---|---|---|---|---|---|---|---|---|---|---|---|
| 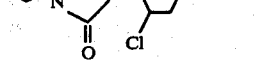 | 0.03 | 0 | 10H | 0 | — | 0 | 0 | 0 | 9H | 0 | 0 | 3H | 2H |
| | 0.06 | 0 | 10H | 2C | — | 2H | 0 | 5H | 10H | 10H | 0 | 5H | 3H |
| | 0.12 | 0 | 10H | 2C | — | 5H | 2H | 10H | 10H | 10H | 0 | 2H | 5H |
|  | 0.12 | 0 | 10E | 0 | — | 5H | 8H | 9H | 10H | 10H | 3H | 4H | 0 |
| | 0.50 | 10H | 10E | 2H | — | 4H | 2H | 10H | 10H | 10H | 3G | 7H | 5H |

TABLE II-continued

PRE-EMERGENCE ON FALLSINGTON SILT LOAM

Structure 1: cyclohexane-fused triazolo with N-aryl where aryl = 2,4-dichloro-5-methoxyphenyl (OCH₃)

| Rate | | | | | | | | | | | | |
|---|---|---|---|---|---|---|---|---|---|---|---|---|
| 0.06 | 0 | 10E | 3C | — | 10C | 0 | 10E | 10E | 10C | 0 | 10H | 5H |
| 0.12 | 7C | 10E | 2C | — | 10C | 0 | 10E | 10E | 10E | 2C | 10H | 8H |
| 0.50 | 6C | 10E | 10C | — | 10C | 10C | 10E | 10E | 10E | 5C | 10H | 10H |

Structure 2: same with OCH₂CH₃ instead of OCH₃

| Rate | | | | | | | | | | | | |
|---|---|---|---|---|---|---|---|---|---|---|---|---|
| 0.06 | 4C | 10C | 0 | 10C | 6C | 0 | 10C | 10C | 8C | 0 | 6H | 5H |
| 0.25 | 5C | 10C | 4C | 10C | 10C | 7C | 10C | 10C | 10C | 8H | 9H | 7H |

EXAMPLE 27

A test to demonstrate the utility of the compounds of the present invention for selective pre-emergence weed control in corn was conducted as follows: 25 cm diameter plastic pots filled with Flanagan silt loam (a prairie soil of approximately 5.5% organic matter content) were planted either to Funk G 4646 corn seeds, planting depth 3.7 cm, or to a variety of weed seeds which were uniformly mixed with the top 2.5 cm layer of soil. The weed species used were: mustard, velvetleaf, jimsonweed, crabgrass, barnyardgrass and giant foxtail. Immediately after planting, the test chemical dissolved in a non-phytotoxic solvent was applied to the bare soil surfaces, each treatment in duplicate. The treated plantings were then held in a greenhouse where they were watered from above on a demand basis. Weed and crop response ratings were made 28 days after treatment and are shown in Table III. The rating system was as described above.

TABLE III

Effectiveness of 2-[2,4-dichloro-5-(1-methylethoxy)-phenyl]-5,6,7,8-tetrahydro-1,2,4-triazolo[4,3-A]-pyridin-3(2H)-one for Selective Pre-emergence Weed Control in Corn Greenhouse Test

| Application Rate, kg/ha | Weeds - Injury Ratings | | | | Response Rating | |
|---|---|---|---|---|---|---|
| | Broad leaves[1] | | Grasses[2] | | Corn[3] | |
| | Rep. I | Rep. II | Rep. I | Rep. II | Rep. I | Rep. II |
| 0.06 | 6C | 6C | 7C | 7C | | |
| 0.12 | 7C | 8C | 8C | 7C | 1C | 1C |
| 0.25 | 9C | 9C | 9C | 9C | 4C | 2C |
| 0.50 | | | | | 4C | 3C |
| 0.75 | | | | | 6C | 7C |
| — | 0 | 0 | 0 | 0 | 0 | 0 |

[1]Mustard, velvetleaf, jimsonweed
[2]Crabgrass, barnyardgrass, giant foxtail
[3]Funk G 4646

EXAMPLE 28

In another test, plastic pots filled with Fallsington silt loam were planted to soybeans, cotton, alfalfa, corn, rice, wheat, sorghum, velvetleaf (*Abutilon theophrasti*), sesbania (*Sesbania exaltata*), cassia (*Cassia tora*), morningglory (*Ipomoea spp.*), jimsonweed (*Datura stramonium*), cocklebur (*Xanthium pennsylvanicum*), crabgrass (*Digitaria spp.*), nutsedge (*Cyperus rotundus*), barnyardgrass (*Echinochloa crusgalli*), giant foxtail (*Setaria faberi*) and wild oats (*Avena fatua*). Eighteen days after planting, the young plants and the soil around them were sprayed overall with the test chemicals dissolved in a non-phytotoxic solvent. Fourteen days after treatment, all species were compared to untreated controls and visually rated for response to treatment. The ratings are again based on a numerical scale extending from 0=no injury, to 10=complete kill. The accompanying descriptive symbols have the following meanings: B=burn; C=chlorosis/necrosis and H=formative effects. The ratings for the compound tested by this procedure are presented in Table IV.

TABLE IV

Over-the-Top Soil/Foliage Treatment

| COMPOUND | Rate, kg/ha | Soy-beans | Vel-vet-leaf | Ses-bania | Cas-sia | Cot-ton | Morn-ing-glory | Al-falfa | Jim-son-weed | Cock-lebur | Corn | Crab-grass | Rice | Nut-sedge | Barn-yard-grass | Wheat | Giant Fox-tail | Wild Oats | Sor-ghum |
|---|---|---|---|---|---|---|---|---|---|---|---|---|---|---|---|---|---|---|---|
| Compound 1: OCH$_3$, dichlorocyclohexyl, triazepinone | 0.12 | 8B | 10B | 10B | 10B | 10B | 9B | 9B | 10B | 7B | 6B | 10C | 5C | 2C | 8B | 4B | 10C | 6C | 6B |
|  | 0.50 | 9B | 10B | 10B | 10B | 10B | 9B | 10B | 10B | 10B | 7B | 10B | 10B | 10B | 10B | 8B | 10B | 9B | 9B |
| Compound 2: (CH$_3$)$_2$CHO-, dichlorocyclohexyl, triazepinone | 0.12 | 7B | 8B | 8B | 8B | 9B | 8B | 4B | 4B | — | 5B | 5B | 6B | 4B | 8B | 4B | 7B | 7B | 10B |
|  | 0.50 | 8B | 10B | 10B | 9B | 10B | 10B | 7B | 10B | — | 7B | 8B | 7B | 6B | 10B | 6B | 8B | 10B | 8B |
| Compound 3: (CH$_3$)$_2$CHO-, dichlorocyclohexyl, triazepinone | 0.12 | 6B | 8B | 9B | 8B | 9B | 8B | 4B | 8B | — | 3B | 2B | 0 | 0 | 4B | 3B | 3B | 5B | 4B |
|  | 0.50 | 7B | — | 10B | 6B | 10B | 10B | 6B | 10B | — | 3B | 5B | 5B | 3B | 6B | 5B | 8B | 6B | 6B |
| Compound 4: OCH$_2$CH$_3$, dichlorocyclohexyl, triazepinone | 0.06 | 8B | 10B | 8B | — | 10B | 9B | 9B | 9B | 3B | 2B | 7B | 3B | 2B | 7B / 5H | 4B | 8B | 3B | 4B |
|  | 0.12 | 8B | 10B | 9B | 5B | 10B | 7B | 10B | 10B | 3B | 3B | 9B | 8B | 3B | 9B / 5H | 5B | 10B | 5B | 4B |
|  | 0.50 | 9B | 10B | 10B | 10B | 10B | 10B | 10B | 10B | 4B | 5B / 3H | 10B | 10B | 7B | 9B / 5H | 5B | 10B | 5B | 10B |
|  |  |  |  |  |  |  |  |  |  |  | 7B / 5H |  |  |  | 10B |  |  |  |  |

EXAMPLE 29

Field grown sugarbeets were treated either pre or postemergence with 3H-1,2,4-triazolo[4,3-a]azepin-3-one, 2-[2,4-dichloro-5-(1-methylethoxy)phenyl]-2,5,6,7,8,9-hexahydro. The data below illustrate the utility of the chemical for weed control in this crop.

| Rate kg/ha | Preemergence | | |
|---|---|---|---|
| | Grasses % Control[1] | Broad leaves % Control[1] | Sugarbeet Crop Injury %[1] |
| 0.125 | 20 | 20 | 0 |
| 0.25 | 35 | 30 | 0 |
| 0.5 | 80 | 50 | 0 |
| 1.0 | 95 | 90 | 10 |

| Rate kg/ha | Postemergence | | |
|---|---|---|---|
| | Grasses % Control[2] | Broad leaves % Control[2] | Sugarbeet Crop Injury %[1] |
| 0.125 | 40 | 70 | 30 |
| 0.25 | 50 | 65 | 30 |
| 0.50 | 75 | 95 | 30 |
| 1.0 | 93 | 99 | 90 |

[1]Taken 6 weeks after treatment.
[2]Taken 3½ weeks after treatment.

EXAMPLE 30

Spring wheat, planted in a silt loam soil was treated preemergence with 2-[2,4-dichloro-5-(1-methylethoxy)-phenyl]-5,6,7,8-tetrahydro-1,2,4-triazolo[4,3-A]-pyridin-3(2H)-one. The data on weed control presented below taken ten weeks after treatment show that the material provides effective weed control.

| Rate kg/ha | % Weed Control | | Wheat Injury % | Wheat Yield % of Control |
|---|---|---|---|---|
| | Grasses | Broad leaves | | |
| 0.06 | 57 | 80 | 0 | 120 |
| 0.125 | 92 | 93 | 0 | 131 |
| 0.25 | 98 | 96 | 10 | 128 |
| 0.50 | 98 | 99 | 57 | 88 |

In a second test, the compound was somewhat more injurious to the crop but weed control was good as shown by the data below taken six weeks after treatment.

| Rate Kg/ha | Weed Control % | | Wheat Injury % |
|---|---|---|---|
| | Grasses | Broad leaves | |
| 0.06 | 20 | 73 | 0 |
| 0.125 | 50 | 90 | 20 |
| 0.25 | 80 | 94 | 50 |
| 0.50 | 92 | 99 | 80 |

What is claimed is:
1. A compound having the formula wherein:

V is hydrogen, fluorine, chlorine, bromine, hydroxy, alkyl of 1–4 carbon atoms or —$OR_1$ wherein:
$R_1$ is alkyl of 1–6 carbon atoms optionally substituted with 1–3 fluorines, chlorines or bromines, cycloalkyl of 4–6 carbon atoms, cycloalkylalkyl of 4–7 carbon atoms, alkenyl of 3–6 carbon atoms optionally substituted with 1–3 fluorines, chlorines or bromines, alkynyl of 3–6 carbon atoms, $CHR_7R_8$ or wherein:
$R_2$ is hydrogen or methyl;
$R_3$ is hydrogen, chlorine, bromine, methyl or methoxy;
$R_4$ is alkyl of 1–4 carbon atoms;
$R_5$ is hydrogen, methyl or methoxy;
$R_6$ is alkyl of 1–4 carbon atoms or alkoxy of 1–4 carbon atoms;
$R_7$ is hydrogen or alkyl of 1–4 carbon atoms; $R_8$ is $CO_2R_9$, $CH_2OR_9$, $CH_2$—$OCR_{10}$, $CN$, —$CCH_3$, —$CH=CHCOR_9$, or —$CN{R_{11} \atop R_{12}}$ $R_9$ is hydrogen or alkyl of 1–4 carbon atoms;
$R_{10}$ is alkyl of 1–3 carbon atoms;
$R_{11}$ is hydrogen, alkyl of 1–4 carbon atoms, alkenyl of 3–4 carbon atoms or alkoxy of 1–2 carbon atoms; and
$R_{12}$ is hydrogen or alkyl of 1–2 carbon atoms
X is fluorine, chlorine, bromine, cyano, methyl methoxy or nitro;
Y is hydrogen, fluorine, chlorine, bromine or methyl;
Z is hydrogen, fluorine, chlorine or bromine;
n is 3, 4 or 5;
m is 0, 1 or 2; and
Q is oxygen or sulfur;
provided that
(1) When V is other than hydrogen, Y must be other than hydrogen;
(2) When m is 1, n is 4 and Y must be other than hydrogen;
(3) When m is 2, n is 4, X and Y are chlorine and V is —$OR_1$ wherein $R_1$ is alkyl of 1–4 carbon atoms;
(4) When Q is sulfur, m is O;
or an agriculturally suitable salt thereof.
2. A compound of claim 1 wherein V is hydrogen, fluorine, chlorine, bromine, hydroxy, methyl or —$OR_1$.
3. A compound of claim 1 wherein X is fluorine, chlorine, bromine, methyl or nitro.
4. A compound of claim 1 wherein Y is fluorine, chlorine, bromine or methyl.
5. A compound of claim 1 wherein Z is hydrogen, fluorine or chlorine.
6. A compound of claim 1 wherein n is 4 or 5.
7. A compound of claim 1 wherein m is 0.
8. A compound of claim 1 wherein independently or in combination V is hydrogen, chlorine, bromine or OR$_1$ and R$_1$ is alkyl of 1-4 carbon atoms; and X is fluorine, chlorine, or bromine; and Y is fluorine, chlorine, bromine or methyl and Z is hydrogen and n is 4 or 5.

9. A compound of claim 8 wherein n is 4.

10. A compound of claim 8 wherein V is hydrogen, chlorine or OR$_1$ and X is chlorine or bromine and Y is fluorine, chlorine or bromine.

11. The compound of claim 1 which is 2-[2,4-dichloro-5-(1-methylethoxy)phenyl]-5,6,7,8-tetrahydro-1,2,4-triazolo[4,3-A]-pyridin-3(2H)-one.

12. The compound of claim 1 which is 2-(2,4-dichloro-5-methoxyphenyl)-5,6,7,8-tetrahydro-1,2,4-triazolo[4,3-A]-pyridin-3(2H)-one.

13. The compound of claim 1 which is 2-(2,4-dichloro-5-ethoxypheny)-5,6,7,8-tetrahydro-1,2,4-triazolo [4,3-A]-pyridin-3(2H)-one.

14. The compound of claim 1 which is 2-[2,4-dichloro-5-(1-methylethoxy)phenyl]-2,5,6,7,8,9-hexahydro-3H-1,2,4-triazolo[4,3-A]-azepin-3-one.

15. The compound of claim 1 which is 2-(2,4-dichloro-5-hydroxyphenyl)-5,6,7,8-tetrahydro-1,2,4-triazolo[4,3-A]pyridin-3(2H)-one.

16. The compound of claim 1 which is 2-(2,4-dichloro-5-propargyloxyphenyl)-5,6,7,8-tetrahydro-1,2,4-triazolo[4,3-A]pyridin-3(2H)-one.

17. A composition for the control of undesirable vegetation consisting essentially of an herbicidally effective amount of a compound of claim 1 and at least one of (a) a surface-active agent and (b) a solid or liquid diluent.

18. A composition for the control of undesirable vegetation consisting essentially of an herbicidally effective amount of a compound of claim 2 and at least one of (a) a surface-active agent and (b) a solid or liquid diluent.

19. A composition for the control of undesirable vegetation consisting essentially of an herbicidally effective amount of a compound of claim 3 and at least one of (a) a surface-active agent and (b) a solid or liquid diluent.

20. A composition for the control of undesirable vegetation consisting essentially of an herbicidally effective amount of a compound of claim 4 and at least one of (a) a surface-active agent and (b) a solid or liquid diluent.

21. A composition for the control of undesirable vegetation consisting essentially of an herbicidally effective amount of a compound of claim 5 and at least one of (a) a surface-active agent and (b) a solid or liquid diluent.

22. A composition for the control of undesirable vegetation consisting essentially of an herbicidally effective amount of a compound of claim 6 and at least one of (a) a surface-active agent and (b) a solid or liquid diluent.

23. A composition for the control of undesirable vegetation consisting essentially of an herbicidally effective amount of a compound of claim 7 and at least one of (a) a surface-active agent and (b) a solid or liquid diluent.

24. A composition for the control of undesirable vegetation consisting essentially of an herbicidally effective amount of a compound of claim 8 and at least one of (a) a surface-active agent and (b) a solid or liquid diluent.

25. A composition for the control of undesirable vegetation consisting essentially of an herbicidally effective amount of a compound of claim 9 and at least one of (a) a surface-active agent and (b) a solid or liquid diluent.

26. A composition for the control of undesirable vegetation consisting essentially of an herbicidally effective amount of a compound of claim 10 and at least one of (a) a surface-active agent and (b) a solid or liquid diluent.

27. A composition for the control of undesirable vegetation consisting essentially of an herbicidally effective amount of the compound of claim 11 and at least one of (a) a surface-active agent and (b) a solid or liquid diluent.

28. A composition for the control of undesirable vegetation consisting essentially of an herbicidally effective amount of the compound of claim 12 and at least one of (a) a surface-active agent and (b) a solid or liquid diluent.

29. A composition for the control of undesirable vegetation consisting essentially of an herbicidally effective amount of the compound of claim 13 and at least one of (a) a surface-active agent and (b) a solid or liquid diluent.

30. A composition for the control of undesirable vegetation consisting essentially of an herbicidally effective amount of the compound of claim 14 and at least one of (a) a surface-active agent and (b) a solid or liquid diluent.

31. A composition for the control of undesirable vegetation consisting essentially of an herbicidally effective amount of the compound of claim 15 and at least one of (a) a surface-active agent and (b) a solid or liquid diluent.

32. A composition for the control of undesirable vegetation consisting essentially of an herbicidally effective amount of the compound of claim 16 and at least one of (a) a surface-active agent and (b) a solid or liquid diluent.

33. A method for the control of undesirable vegetation comprising applying to the locus of such undesirable vegetation a herbicidally effective amount of a compound of claim 1.

34. A method for the control of undesirable vegetation comprising applying to the locus of such undesirable vegetation a herbicidally effective amount of a compound of claim 2.

35. A method for the control of undesirable vegetation comprising applying to the locus of such undesirable vegetation a herbicidally effective amount of a compound of claim 3.

36. A method for the control of undesirable vegetation comprising applying to the locus of such undesirable vegetation a herbicidally effective amount of a compound of claim 4.

37. A method for the control of undesirable vegetation comprising applying to the locus of such undesirable vegetation a herbicidally effective amount of a compound of claim 5.

38. A method for the control of undesirable vegetation comprising applying to the locus of such undesirable vegetation a herbicidally effective amount of a compound of claim 6.

39. A method for the control of undesirable vegetation comprising applying to the locus of such undesirable vegetation a herbicidally effective amount of a compound of claim 7.

40. A method for the control of undesirable vegetation comprising applying to the locus of such undesirable vegetation a herbicidally effective amount of a compound of claim 8.

41. A method for the control of undesirable vegetation comprising applying to the locus of such undesirable vegetation a herbicidally effective amount of a compound of claim 9.

42. A method for the control of undesirable vegetation comprising applying to the locus of such undesirable vegetation a herbicidally effective amount of a compound of claim 10.

43. A method for the control of undesirable vegetation comprising applying to the locus of such undesirable vegetation a herbicidally effective amount of the compound of claim 11.

44. A method for the control of undesirable vegetation comprising applying to the locus of such undesirable vegetation a herbicidally effective amount of the compound of claim 12.

45. A method for the control of undesirable vegetation comprising applying to the locus of such undesirable vegetation a herbicidally effective amount of the compound of claim 13.

46. A method for the control of undesirable vegetation comprising applying to the locus such undesirable vegetation a herbicidally effective amount of the compound of claim 14.

47. A method for the control of undesirable vegetation comprising applying to the locus of such undesirable vegetation a herbicidally effective amount of the compound of claim 15.

48. A method for the control of undesirable vegetation comprising applying to the locus of such undesirable vegetation a herbicidally effective amount of the compound of claim 16.

49. A method for the control of undesirable vegetation in crops comprising applying to the locus of such undesirable vegetation a herbicidally effective amount of a compound of claim 1.

50. A method for the control of undesirable vegetation in crops comprising applying to the locus of such undesirable vegetation a herbicidally effective amount of a compound of claim 2.

51. A method for the control of undesirable vegetation in crops comprising applying to the locus of such undesirable vegetation a herbicidally effective amount of a compound of claim 3.

52. A method for the control of undesirable vegetation in crops comprising applying to the locus of such undesirable vegetation a herbicidally effective amount of a compound of claim 4.

53. A method for the control of undesirable vegetation in crops comprising applying to the locus of such undesirable vegetation a herbicidally effective amount of a compound of claim 5.

54. A method for the control of undesirable vegetation in crops comprising applying to the locus of such undesirable vegetation a herbicidally effective amount of a compound of claim 6.

55. A method for the control of undesirable vegetation in crops comprising applying to the locus of such undesirable vegetation a herbicidally effective amount of a compound of claim 7.

56. A method for the control of undesirable vegetation in crops comprising applying to the locus of such undesirable vegetation a herbicidally effective amount of a compound of claim 8.

57. A method for the control of undesirable vegetation in crops comprising applying to the locus of such undesirable vegetation a herbicidally effective amount of a compound of claim 9.

58. A method for the control of undesirable vegetation in crops comprising applying to the locus of such undesirable vegetation in herbicidally effective amount of a compound of claim 10.

59. A method for the control of undesirable vegetation in crops comprising applying to the locus of such undesirable vegetation a herbicidally effective amount of the compound of claim 11.

60. A method for the control of undesirable vegetation in crops comprising applying to the locus of such undesirable vegetation a herbicidally effective amount of the compound of claim 12.

61. A method for the control of undesirable vegetation in crops comprising applying to the locus of such undesirable vegetation a herbicidally effective amount of the compound of claim 13.

62. A method for the control of undesirable vegetation in crops comprising applying to the locus of such undesirable vegetation a herbicidally effective amount of the compound of claim 14.

63. A method for the control of undesirable vegetation in crops comprising applying to the locus of such undesirable vegetation a herbicidally effective amount of the compound of claim 15.

64. A method for the control of undesirable vegetation in crops comprising applying to the locus of such undesirable vegetation a herbicidally effective amount of the compound of claim 16.

* * * * *